(12) United States Patent  (10) Patent No.: US 7,644,714 B2
Atkinson et al.  (45) Date of Patent: Jan. 12, 2010

(54) DEVICES AND METHODS FOR TREATING SLEEP DISORDERS

(75) Inventors: Robert E. Atkinson, White Bear Lake, MN (US); Chad J. Kugler, Andover, MN (US)

(73) Assignee: Apnex Medical, Inc., Minneapolis, MN (US)

( * ) Notice: Subject to any disclaimer, the term of this patent is extended or adjusted under 35 U.S.C. 154(b) by 290 days.

(21) Appl. No.: 11/438,330

(22) Filed: May 23, 2006

(65) Prior Publication Data

US 2006/0266369 A1  Nov. 30, 2006

Related U.S. Application Data

(60) Provisional application No. 60/685,513, filed on May 27, 2005, provisional application No. 60/717,337, filed on Sep. 15, 2005.

(51) Int. Cl.
*A61F 5/56* (2006.01)
(52) U.S. Cl. ........................... 128/848; 602/902
(58) Field of Classification Search ................. 128/848, 128/898, 897, 860, 899; 600/12, 37; 602/902; 606/60, 263, 264
See application file for complete search history.

(56) References Cited

U.S. PATENT DOCUMENTS

| 758,030 | A | 4/1904 | Carence |
|---|---|---|---|
| 1,520,930 | A | 12/1924 | Calhoun |
| 1,701,277 | A | 2/1929 | Shindel |
| 1,914,418 | A | 6/1933 | Goyena |
| 2,046,664 | A | 7/1936 | Weaver |
| 2,151,227 | A | 3/1939 | Pawelek |
| 2,237,954 | A | 4/1941 | Wilson |
| 2,241,444 | A | 5/1941 | Bower |
| 2,243,360 | A | 5/1941 | Slatis |
| 2,274,886 | A | 3/1942 | Carroll |
| 2,526,586 | A | 10/1950 | Shuff |
| 2,693,799 | A | 11/1954 | Herman |
| 2,777,442 | A | 1/1957 | Zelano |
| 2,928,388 | A | 3/1960 | Jaroslaw |
| 3,457,917 | A | 7/1969 | Mercurio |
| 3,513,839 | A | 5/1970 | Vacante |
| 3,680,555 | A | 8/1972 | Warncke |
| 3,722,509 | A | 3/1973 | Nebel |

(Continued)

FOREIGN PATENT DOCUMENTS

EP  0 330 740 A2  9/1989

(Continued)

OTHER PUBLICATIONS

Arie Oliven et al., Upper airway response to electrical stimulation of the genioglossus in obstructive sleep apnea, Journal of Applied Physiology 95:2023-2029, 2003.

(Continued)

*Primary Examiner*—Patricia M Bianco
*Assistant Examiner*—James M Robinson
(74) *Attorney, Agent, or Firm*—Finnegan, Henderson, Farabow, Garrett and Dunner L.L.P.

(57) ABSTRACT

Devices and methods for maintaining an open airway are described. Systems and methods are described for maintaining an opening of an airway by application of force to a patient's tissues in one of inferior, anterior, and lateral directions.

51 Claims, 21 Drawing Sheets

U.S. PATENT DOCUMENTS

| | | |
|---|---|---|
| 3,774,618 A | 11/1973 | Avery |
| 3,865,106 A | 2/1975 | Palush |
| 3,884,223 A | 5/1975 | Keindl |
| 3,906,936 A | 9/1975 | Habal |
| 4,220,150 A | 9/1980 | King |
| 4,221,217 A | 9/1980 | Amezcua |
| 4,257,407 A | 3/1981 | Macchi |
| 4,267,831 A | 5/1981 | Aguilar |
| 4,374,527 A | 2/1983 | Iversen |
| 4,567,892 A | 2/1986 | Plicchi et al. |
| 4,573,481 A | 3/1986 | Bullara |
| 4,657,003 A | 4/1987 | Wirtz |
| 4,777,963 A | 10/1988 | McKenna |
| 4,830,008 A | 5/1989 | Meer |
| 4,899,750 A | 2/1990 | Eckwall |
| 4,915,105 A | 4/1990 | Lee |
| 4,919,136 A | 4/1990 | Alt |
| 4,940,065 A | 7/1990 | Tanagho et al. |
| 4,960,133 A | 10/1990 | Hewson |
| 4,978,323 A | 12/1990 | Freedman |
| 4,996,983 A | 3/1991 | AmRhein |
| 5,016,808 A | 5/1991 | Heil, Jr. et al. |
| 5,076,259 A | 12/1991 | Hayek |
| 5,101,808 A | 4/1992 | Kobayashi et al. |
| 5,105,826 A | 4/1992 | Smits et al. |
| 5,117,819 A | 6/1992 | Servidio et al. |
| 5,121,754 A | 6/1992 | Mullett |
| 5,123,425 A | 6/1992 | Shannon, Jr. et al. |
| 5,133,354 A | 7/1992 | Kallok |
| 5,146,918 A | 9/1992 | Kallok et al. |
| 5,158,080 A | 10/1992 | Kallok |
| 5,174,287 A | 12/1992 | Kallok et al. |
| 5,176,618 A | 1/1993 | Freedman |
| 5,178,156 A | 1/1993 | Takishima et al. |
| 5,190,053 A | 3/1993 | Meer |
| 5,211,173 A | 5/1993 | Kallok et al. |
| 5,215,082 A | 6/1993 | Kallok et al. |
| 5,222,478 A | 6/1993 | Scarberry et al. |
| 5,239,995 A | 8/1993 | Estes et al. |
| 5,277,193 A | 1/1994 | Takishima et al. |
| 5,281,219 A | 1/1994 | Kallok et al. |
| 5,300,094 A | 4/1994 | Kallok et al. |
| 5,324,321 A | 6/1994 | Pohndorf et al. |
| 5,335,657 A | 8/1994 | Terry, Jr. et al. |
| 5,343,878 A | 9/1994 | Scarberry et al. |
| 5,344,438 A | 9/1994 | Testerman et al. |
| 5,388,578 A | 2/1995 | Yomtov et al. |
| 5,392,773 A | 2/1995 | Bertrand |
| 5,417,205 A | 5/1995 | Wang |
| 5,425,359 A | 6/1995 | Liou |
| 5,458,629 A | 10/1995 | Baudino et al. |
| 5,483,969 A | 1/1996 | Testerman et al. |
| 5,485,836 A | 1/1996 | Lincoln |
| 5,485,851 A | 1/1996 | Erickson |
| 5,511,543 A | 4/1996 | Shirley |
| 5,522,382 A | 6/1996 | Sullivan et al. |
| 5,522,862 A | 6/1996 | Testerman et al. |
| 5,531,778 A | 7/1996 | Maschino et al. |
| 5,540,732 A | 7/1996 | Testerman |
| 5,540,733 A | 7/1996 | Testerman et al. |
| 5,540,734 A | 7/1996 | Zabara |
| 5,546,938 A | 8/1996 | McKenzie |
| 5,549,655 A | 8/1996 | Erickson |
| 5,555,900 A | 9/1996 | Rich |
| 5,568,808 A | 10/1996 | Rimkus |
| 5,591,216 A | 1/1997 | Testerman et al. |
| 5,611,333 A | 3/1997 | Johnson |
| 5,630,411 A | 5/1997 | Holscher |
| 5,653,224 A | 8/1997 | Johnson |
| 5,682,881 A | 11/1997 | Winthrop et al. |
| 5,697,105 A | 12/1997 | White |
| 5,697,363 A | 12/1997 | Hart |
| 5,730,122 A | 3/1998 | Lurie |
| 5,740,798 A | 4/1998 | McKinney |
| 5,752,511 A | 5/1998 | Simmons et al. |
| 5,752,524 A | 5/1998 | Corcoran |
| 5,755,232 A | 5/1998 | Kalt |
| 5,787,884 A | 8/1998 | Tovey |
| 5,820,572 A | 10/1998 | Palmer |
| 5,848,589 A | 12/1998 | Welnetz |
| 5,855,552 A | 1/1999 | Houser et al. |
| 5,890,491 A | 4/1999 | Rimkus |
| 5,895,360 A | 4/1999 | Christopherson et al. |
| 5,922,014 A | 7/1999 | Warman et al. |
| 5,938,596 A | 8/1999 | Woloszko et al. |
| 5,944,680 A | 8/1999 | Christopherson et al. |
| 5,947,119 A | 9/1999 | Reznick |
| 5,972,000 A | 10/1999 | Beyar et al. |
| 5,979,456 A | 11/1999 | Magovern |
| 5,988,166 A | 11/1999 | Hayek |
| 5,988,171 A * | 11/1999 | Sohn et al. .................. 128/848 |
| 6,010,459 A | 1/2000 | Silkoff et al. |
| 6,015,389 A | 1/2000 | Brown |
| 6,021,352 A | 2/2000 | Christopherson et al. |
| 6,021,354 A | 2/2000 | Warman et al. |
| 6,029,667 A | 2/2000 | Lurie |
| 6,041,780 A | 3/2000 | Richard |
| 6,066,165 A | 5/2000 | Racz |
| 6,098,624 A | 8/2000 | Utamaru |
| 6,109,262 A | 8/2000 | Tovey |
| 6,119,690 A | 9/2000 | Pentaleo |
| 6,126,611 A | 10/2000 | Bourgeois et al. |
| 6,132,384 A | 10/2000 | Christopherson et al. |
| 6,161,541 A | 12/2000 | Woodson |
| 6,198,970 B1 | 3/2001 | Freed et al. |
| 6,201,994 B1 | 3/2001 | Warman et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,240,316 B1 | 5/2001 | Richmond et al. |
| 6,244,267 B1 | 6/2001 | Eifrig |
| 6,251,126 B1 | 6/2001 | Ottenhoff et al. |
| 6,269,269 B1 | 7/2001 | Ottenhoff et al. |
| 6,345,202 B2 | 2/2002 | Richmond et al. |
| 6,366,815 B1 | 4/2002 | Haugland et al. |
| 6,378,525 B1 | 4/2002 | Beyar et al. |
| 6,460,539 B1 | 10/2002 | Japuntich et al. |
| 6,484,725 B1 | 11/2002 | Chi |
| 6,511,458 B2 | 1/2003 | Milo et al. |
| 6,514,217 B1 | 2/2003 | Selmon et al. |
| 6,561,188 B1 | 5/2003 | Ellis |
| 6,587,725 B1 | 7/2003 | Durand et al. |
| 6,600,956 B2 | 7/2003 | Maschino et al. |
| 6,606,521 B2 | 8/2003 | Paspa et al. |
| 6,626,179 B1 | 9/2003 | Pedley |
| 6,636,767 B1 | 10/2003 | Knudson et al. |
| 6,641,542 B2 | 11/2003 | Cho et al. |
| 6,647,289 B2 | 11/2003 | Prutchi |
| 6,651,652 B1 | 11/2003 | Ward |
| 6,656,194 B1 * | 12/2003 | Gannoe et al. ............... 606/153 |
| 6,668,834 B1 | 12/2003 | Zikria |
| 6,718,982 B2 | 4/2004 | Smith et al. |
| 6,719,725 B2 | 4/2004 | Milo et al. |
| 6,770,022 B2 | 8/2004 | Mechlenburg et al. |
| 6,776,162 B2 | 8/2004 | Wood |
| 6,799,575 B1 | 10/2004 | Carter |
| 6,819,958 B2 | 11/2004 | Weiner et al. |
| 6,829,503 B2 | 12/2004 | Alt |
| 6,829,508 B2 | 12/2004 | Schulman et al. |
| RE38,705 E | 2/2005 | Hill et al. |
| 6,881,192 B1 | 4/2005 | Park |
| 6,883,518 B2 | 4/2005 | Mittelstadt et al. |
| 6,890,306 B2 | 5/2005 | Poezevera |
| 6,904,320 B2 | 6/2005 | Park et al. |

| Patent/Publication | Date | Name |
|---|---|---|
| 6,907,295 B2 | 6/2005 | Gross et al. |
| 6,928,324 B2 | 8/2005 | Park et al. |
| 6,935,335 B1 | 8/2005 | Lehrman et al. |
| 6,955,172 B2 | 10/2005 | Nelson et al. |
| 6,978,171 B2 | 12/2005 | Goetz et al. |
| 6,997,177 B2 | 2/2006 | Wood |
| 7,027,869 B2 | 4/2006 | Danek et al. |
| 7,054,692 B1 | 5/2006 | Whitehurst et al. |
| 7,065,410 B2 | 6/2006 | Bardy et al. |
| 7,073,505 B2 | 7/2006 | Nelson et al. |
| 7,082,331 B1 | 7/2006 | Park et al. |
| 7,089,932 B2 | 8/2006 | Dodds |
| 7,094,206 B2 | 8/2006 | Hoffman |
| 7,117,036 B2 | 10/2006 | Florio |
| 7,128,717 B1 | 10/2006 | Thatch et al. |
| 7,149,573 B2 | 12/2006 | Wang |
| 7,152,604 B2 | 12/2006 | Hickle et al. |
| 7,155,278 B2 | 12/2006 | King et al. |
| 7,156,098 B2 | 1/2007 | Dolezal et al. |
| 7,160,252 B2 | 1/2007 | Cho |
| 7,160,255 B2 | 1/2007 | Saadat |
| 7,178,524 B2 | 2/2007 | Noble |
| 7,188,627 B2 | 3/2007 | Nelson et al. |
| 7,216,648 B2 | 5/2007 | Nelson et al. |
| 7,302,951 B2 | 12/2007 | Mittelstadt et al. |
| 7,360,542 B2 | 4/2008 | Nelson et al. |
| 7,367,340 B2 | 5/2008 | Nelson et al. |
| 7,441,559 B2 | 10/2008 | Nelson et al. |
| 2001/0010010 A1 | 7/2001 | Richmond et al. |
| 2001/0031929 A1 | 10/2001 | O'Toole |
| 2002/0010495 A1 | 1/2002 | Freed et al. |
| 2002/0049479 A1 | 4/2002 | Pitts |
| 2002/0092527 A1 | 7/2002 | Wood |
| 2002/0128700 A1 | 9/2002 | Cross |
| 2002/0166556 A1 | 11/2002 | Jacob |
| 2002/0195108 A1 | 12/2002 | Mittelstadt et al. |
| 2002/0195109 A1 | 12/2002 | Mittelstadt et al. |
| 2003/0034031 A1 | 2/2003 | Lev et al. |
| 2003/0083696 A1 | 5/2003 | Avital |
| 2003/0093128 A1 | 5/2003 | Freed et al. |
| 2003/0106555 A1 | 6/2003 | Tovey |
| 2003/0106556 A1 | 6/2003 | Alperovich et al. |
| 2003/0114905 A1 | 6/2003 | Kuzma |
| 2003/0167018 A1 | 9/2003 | Wyckoff |
| 2003/0195571 A1 | 10/2003 | Burnes et al. |
| 2003/0209145 A1 | 11/2003 | Soper |
| 2003/0216789 A1 | 11/2003 | Deem et al. |
| 2004/0015204 A1 | 1/2004 | Whitehurst et al. |
| 2004/0020489 A1 | 2/2004 | Gillispie et al. |
| 2004/0045555 A1 | 3/2004 | Nelson et al. |
| 2004/0045556 A1 | 3/2004 | Nelson et al. |
| 2004/0049102 A1 | 3/2004 | Nelson et al. |
| 2004/0049241 A1 | 3/2004 | Campos |
| 2004/0055603 A1 | 3/2004 | Bruce |
| 2004/0073272 A1 | 4/2004 | Knudson et al. |
| 2004/0089303 A1 | 5/2004 | Chien |
| 2004/0089313 A1* | 5/2004 | Utley et al. ............ 128/898 |
| 2004/0111139 A1 | 6/2004 | McCreery |
| 2004/0116819 A1 | 6/2004 | Alt |
| 2004/0139975 A1* | 7/2004 | Nelson et al. ............ 128/848 |
| 2004/0149290 A1 | 8/2004 | Nelson et al. |
| 2004/0162499 A1 | 8/2004 | Nagai et al. |
| 2004/0194784 A1 | 10/2004 | Bertrand |
| 2004/0215288 A1 | 10/2004 | Lee et al. |
| 2004/0233058 A1 | 11/2004 | Dodds |
| 2004/0260310 A1 | 12/2004 | Harris |
| 2004/0261791 A1 | 12/2004 | Horian |
| 2005/0004417 A1 | 1/2005 | Nelson et al. |
| 2005/0004610 A1 | 1/2005 | Kim et al. |
| 2005/0010265 A1 | 1/2005 | Fassio et al. |
| 2005/0038490 A1 | 2/2005 | Gross et al. |
| 2005/0039757 A1 | 2/2005 | Wood |
| 2005/0043644 A1 | 2/2005 | Stahmann et al. |
| 2005/0043772 A1 | 2/2005 | Stahmann et al. |
| 2005/0076908 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0085874 A1 | 4/2005 | Davis et al. |
| 2005/0092334 A1* | 5/2005 | Conrad et al. ............ 128/898 |
| 2005/0098176 A1 | 5/2005 | Hoffrichter |
| 2005/0101833 A1 | 5/2005 | Hsu et al. |
| 2005/0119711 A1 | 6/2005 | Cho et al. |
| 2005/0126563 A1 | 6/2005 | van der Burg et al. |
| 2005/0139216 A1 | 6/2005 | Mittelstadt et al. |
| 2005/0159637 A9 | 7/2005 | Nelson et al. |
| 2005/0165457 A1 | 7/2005 | Benser et al. |
| 2005/0209513 A1 | 9/2005 | Heruth et al. |
| 2005/0209643 A1 | 9/2005 | Heruth et al. |
| 2005/0234523 A1 | 10/2005 | Levin et al. |
| 2005/0235992 A1 | 10/2005 | Djupesland |
| 2005/0240241 A1 | 10/2005 | Yun et al. |
| 2005/0251080 A1* | 11/2005 | Hyde, Jr. ............ 602/26 |
| 2005/0251216 A1 | 11/2005 | Hill et al. |
| 2005/0261747 A1 | 11/2005 | Schuler et al. |
| 2005/0267380 A1 | 12/2005 | Poezevara |
| 2005/0267547 A1 | 12/2005 | Knudson et al. |
| 2005/0274387 A1 | 12/2005 | MacKen |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0004429 A1 | 1/2006 | Mrva et al. |
| 2006/0005842 A1 | 1/2006 | Rashad et al. |
| 2006/0005843 A9 | 1/2006 | Nelson et al. |
| 2006/0025828 A1 | 2/2006 | Armstrong et al. |
| 2006/0030919 A1 | 2/2006 | Mrva et al. |
| 2006/0032497 A1 | 2/2006 | Doshi |
| 2006/0041295 A1 | 2/2006 | Osypka |
| 2006/0052836 A1 | 3/2006 | Kim et al. |
| 2006/0058588 A1 | 3/2006 | Zdeblick |
| 2006/0058792 A1* | 3/2006 | Hynes ............ 606/61 |
| 2006/0058852 A1 | 3/2006 | Koh et al. |
| 2006/0064029 A1 | 3/2006 | Arad |
| 2006/0064138 A1 | 3/2006 | Velasco et al. |
| 2006/0070626 A1 | 4/2006 | Frazier et al. |
| 2006/0079802 A1 | 4/2006 | Jensen et al. |
| 2006/0095088 A1 | 5/2006 | De Ridder |
| 2006/0111755 A1 | 5/2006 | Stone et al. |
| 2006/0116739 A1 | 6/2006 | Betser et al. |
| 2006/0129189 A1 | 6/2006 | George et al. |
| 2006/0135886 A1 | 6/2006 | Lippert et al. |
| 2006/0136024 A1 | 6/2006 | Cohen et al. |
| 2006/0142815 A1 | 6/2006 | Tehrani et al. |
| 2006/0144398 A1 | 7/2006 | Doshi et al. |
| 2006/0149345 A1 | 7/2006 | Boggs et al. |
| 2006/0150978 A1 | 7/2006 | Doshi et al. |
| 2006/0150979 A1 | 7/2006 | Doshi et al. |
| 2006/0150980 A1 | 7/2006 | Kim |
| 2006/0150986 A1 | 7/2006 | Roue et al. |
| 2006/0167497 A1 | 7/2006 | Armstrong et al. |
| 2006/0184204 A1 | 8/2006 | He |
| 2006/0195170 A1 | 8/2006 | Cohen et al. |
| 2006/0201519 A1 | 9/2006 | Frazier et al. |
| 2006/0207606 A1 | 9/2006 | Roue et al. |
| 2006/0207607 A1 | 9/2006 | Hirotsuka et al. |
| 2006/0207608 A1 | 9/2006 | Hirotsuka et al. |
| 2006/0207612 A1 | 9/2006 | Jackson et al. |
| 2006/0211951 A1 | 9/2006 | Milijasevic et al. |
| 2006/0224209 A1 | 10/2006 | Meyer |
| 2006/0224211 A1 | 10/2006 | Durand |
| 2006/0241506 A1 | 10/2006 | Melker et al. |
| 2006/0241708 A1 | 10/2006 | Boute |
| 2006/0247729 A1 | 11/2006 | Tehrani et al. |
| 2006/0259079 A1 | 11/2006 | King |
| 2006/0264777 A1 | 11/2006 | Drew |

| | | | |
|---|---|---|---|
| 2006/0266369 A1 | 11/2006 | Atkinson et al. |
| 2006/0270889 A1 | 11/2006 | Nelson et al. |
| 2006/0271118 A1 | 11/2006 | Libbus et al. |
| 2006/0271137 A1 | 11/2006 | Stanton-Hicks |
| 2006/0282127 A1 | 12/2006 | Zealear |
| 2006/0289014 A1 | 12/2006 | Purdy et al. |
| 2006/0289015 A1 | 12/2006 | Boucher et al. |
| 2006/0293720 A1 | 12/2006 | DiLorenzo |
| 2006/0293723 A1 | 12/2006 | Whitehurst et al. |
| 2007/0000497 A1 | 1/2007 | Boucher et al. |
| 2007/0021785 A1 | 1/2007 | Inman et al. |
| 2007/0027482 A1 | 2/2007 | Parnis et al. |
| 2007/0034210 A1 | 2/2007 | Paraschac et al. |
| 2007/0038265 A1 | 2/2007 | Tcheng et al. |
| 2007/0043411 A1 | 2/2007 | Foster et al. |
| 2007/0089756 A1 | 4/2007 | Nelson et al. |
| 2007/0095347 A1 | 5/2007 | Lampotang et al. |
| 2007/0102004 A1 | 5/2007 | Nelson et al. |
| 2007/0119463 A1 | 5/2007 | Nelson et al. |
| 2007/0125379 A1 | 6/2007 | Pierro et al. |
| 2007/0137654 A1 | 6/2007 | Paraschac et al. |
| 2007/0137655 A1 | 6/2007 | Paraschac et al. |
| 2007/0144531 A1 | 6/2007 | Tomas et al. |
| 2007/0144532 A1 | 6/2007 | Gillis et al. |
| 2007/0144533 A1 | 6/2007 | Nelson et al. |
| 2007/0144539 A1 | 6/2007 | van der Burg et al. |
| 2007/0175478 A1 | 8/2007 | Brunst |
| 2007/0186936 A1 | 8/2007 | Nelson et al. |
| 2007/0193587 A1 | 8/2007 | Boucher et al. |
| 2007/0209664 A1 | 9/2007 | Paraschac et al. |
| 2007/0209665 A1 | 9/2007 | Gillis et al. |
| 2007/0227542 A1 | 10/2007 | Kashmakov et al. |
| 2007/0256693 A1 | 11/2007 | Paraschac et al. |
| 2007/0267027 A1 | 11/2007 | Nelson et al. |
| 2007/0270631 A1 | 11/2007 | Nelson et al. |
| 2007/0270632 A1 | 11/2007 | Nelson et al. |
| 2007/0272257 A1 | 11/2007 | Nelson et al. |
| 2007/0277832 A1 | 12/2007 | Doshi et al. |
| 2007/0283692 A1 | 12/2007 | Tetsuka et al. |
| 2007/0283962 A1 | 12/2007 | Doshi et al. |
| 2007/0295338 A1 | 12/2007 | Loomas et al. |
| 2008/0023007 A1 | 1/2008 | Dolezal et al. |
| 2008/0023012 A1 | 1/2008 | Dineen et al. |
| 2008/0027480 A1 | 1/2008 | van der Burg et al. |
| 2008/0027560 A1 | 1/2008 | Jackson et al. |
| 2008/0035160 A1 | 2/2008 | Woodson et al. |
| 2008/0041373 A1 | 2/2008 | Doshi et al. |
| 2008/0053461 A1 | 3/2008 | Hirotsuka et al. |
| 2008/0058584 A1 | 3/2008 | Hirotsuka et al. |
| 2008/0060660 A1 | 3/2008 | Nelson et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0066769 A1 | 3/2008 | Dineen et al. |
| 2008/0163875 A1 | 7/2008 | Aarestad et al. |
| 2008/0221684 A1 | 9/2008 | Nelson et al. |

FOREIGN PATENT DOCUMENTS

| | | |
|---|---|---|
| EP | 0 892 926 B1 | 6/2002 |
| EP | 0 900 102 B1 | 7/2004 |
| EP | 1 404 221 B1 | 2/2007 |
| EP | 1 854 494 A1 | 11/2007 |
| EP | 1 322 384 B1 | 12/2007 |
| JP | 53118893 | 10/1978 |
| JP | 9-294819 | 11/1997 |
| JP | 2000-506601 | 5/2000 |
| JP | 2000-508562 | 7/2000 |
| JP | 2003-305135 | 10/2003 |
| JP | 2004-508908 | 3/2004 |
| JP | 2004-532707 | 10/2004 |
| JP | 3688301 | 6/2005 |
| JP | 2005-521485 | 7/2005 |
| JP | 2007-21156 | 2/2007 |
| WO | WO 96/34586 | 11/1996 |
| WO | WO 96/40335 | 12/1996 |
| WO | WO 98/20938 | 5/1998 |
| WO | WO 03/000347 A1 | 1/2003 |
| WO | WO 03/006095 A1 | 1/2003 |
| WO | WO 03/082393 A1 | 10/2003 |
| WO | WO 2005/004993 A1 | 1/2005 |
| WO | WO 2006/045251 A1 | 5/2006 |
| WO | WO 2006/063339 A2 | 6/2006 |
| WO | WO 2007/134458 A1 | 11/2007 |

OTHER PUBLICATIONS

Alan R. Schwartz, Effect of Electrical Stimulation of the Hypoglossal Nerve on Airflow Mechanics in the Isolated Upper Airway, American Review of Respiratory Disease, University of Minnesota Bio-Medical Library, vol. 147, No. 5, pp. 1144-1150, May 1993.

Paul E. Ciske and John A. Faulkner, Chronic electrical Stimulation of nongrafted and grafted skeletal muscles in rats, J. Appl. Physiol. 59(5): 1434-1439, 1985.

Hiroshi Miki et al., Effects of Electrical Stimulation of the Genioglossus on Upper Airway Resistance in Anesthetized Dogs, American Thoracic Society, vol. 140, No. 5, Nov. 1989, pp. 1279-1284.

Hiroshi Miki et al., Effect of Electrical Stimulation of Genioglossus Muscle on Upper Airway Resistance in Anesthetized Dogs, Tohoku J. Exp. Med., 1987, 153, 397-398.

Hiroshi Miki et al., Effects of Submental Electrical Stimulation During Sleep on Upper Airway Patency in Patients with Obstructive Sleep Apnea, American Thoracic Society, vol. 140, No. 5, Nov. 1989, pp. 1285-1289.

Hiroshi Miki, A New Treatment for Obstructive Sleep Apnea Syndrome by Electrical Stimulation of Submental Region, Tohoku J. Exp. Med., 1988, 154, 91-92.

Spence et al., "High-flow nasal cannula as a device to provide continuous positive airway pressure in infants," *Journal of Perinatology*, Dec. 2007, pp. 772-775, vol. 27 (12), Nature Publishing Group.

Kirkness et al., "Nasal airflow dynamics: mechanisms and responses associated with an external nasal dilator strip," University of Western Sydney, T.C. Amis School of Science, Department of Respiratory Medicine, Westmead Hospital and University of Sydney, Westmead, Australia, 2000.

De Almedia et al., "Nasal pressure recordings to detect obstructive sleep apnea," *Sleep and Breathing*, Feb. 25, 2006, pp. 62-69, vol. 10 (2), Springer Heidelberg.

Saslow et al., "Work of breathing using high-flow nasal cannula in preterm infants," *Journal of Perinatology*, May 11, 2006, pp. 476-480, vol. 26 (8), Nature Publishing Group.

Campbell et al., "Nasal Continuous positive airway pressure from high flow cannula versus Infant Flow for preterm infants," *Journal of Perinatoloqy*, Jul. 2006, pp. 546-549, vol. 26 (9), Nature Publishing Group.

Trevisanuto et al., "A new device for administration of continuous positive airway pressure in preterm infants: comparison with a standard nasal CPAP continuous positive airway pressure system," *Intensive Care Medicine*, Apr. 2005, pp. 859-864, vol. 31 (6), Springer-Verlag.

Verse et al., "New developments in the therapy of obstructive sleep apnea," *European Archives of Oto-Rhino-Laryngology*, Jan. 2001, pp. 31-37, vol. 258 (1), Springer-Verlag.

Paquereau et al., "Positive pressure titration in the treatment of obstructive sleep apnea syndrome using continuous airway positive pressure," *Revue Des Maladies Respiratoires*, Apr. 2000, pp. 459-465, vol. 17 (2). Masson Editeur, Abstract.

Mahadevia et al., "Effects of expiratory positive airway pressure on sleep-induced respiratory abnormalities in patients with hypersomnia-sleep apnea syndrome," *Am. Rev. Respir. Dis.*, Feb. 1983, vol. 128, pp. 708-711.

Tiran et al., "An Improved Device for Posterior Rhinomanometry to Measure Nasal Resistance," *Journal of Biomechanical Engineering*, Nov. 2005, vol. 127, pp. 994-997.

Noseda et al., "Compliance with nasal continuous positive airway pressure assessed with a pressure monitor: pattern of use and influence of sleep habits," Chest Clinics and Sleep Laboratories, Hôpitaux Erasme et Brugmann, Université Libre de Bruxelles, Brussels, Belgium, 2000, vol. 94, pp. 76-81.

Goding Jr. et al., "Relief of Upper Airway Obstruction With Hypoglossal Nerve Stimulation in the Canine," *The Laryngoscope*, Feb. 1998, pp. 162-169, vol. 108, Lippincott-Raven Publishers, U.S.A.

* cited by examiner

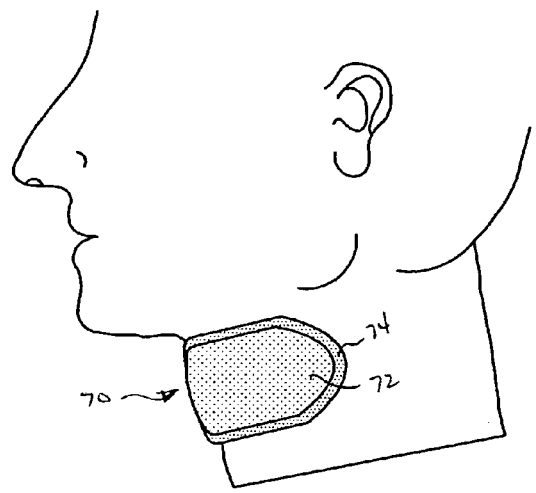
FIG. 7A
FIG. 7C
FIG. 7D
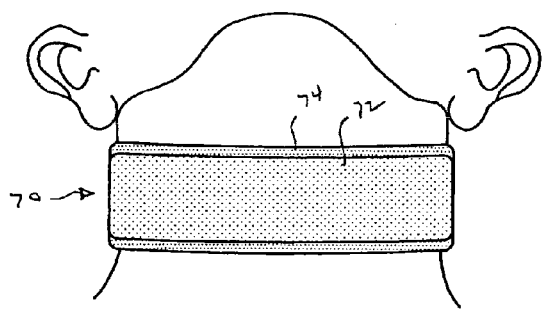
FIG. 7B

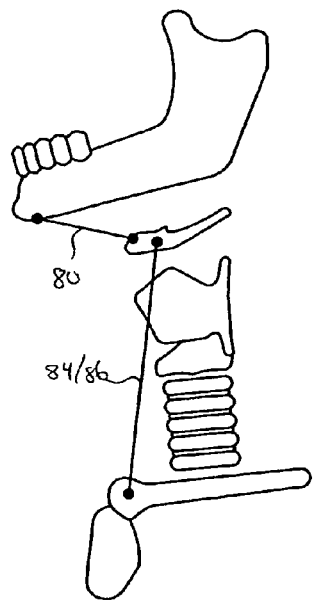
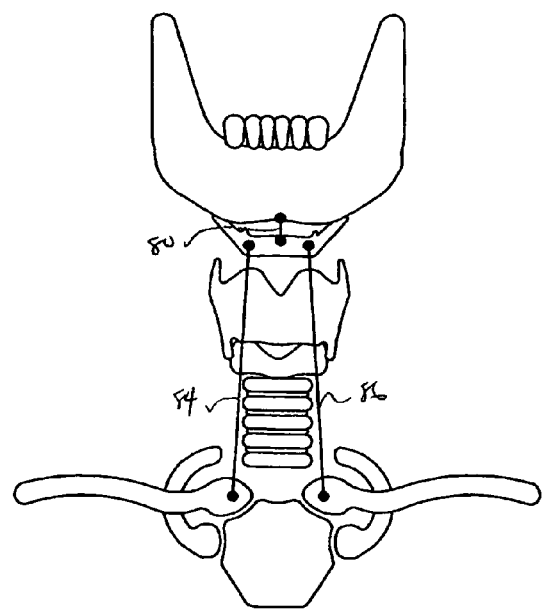
FIG. 8E  FIG. 8F
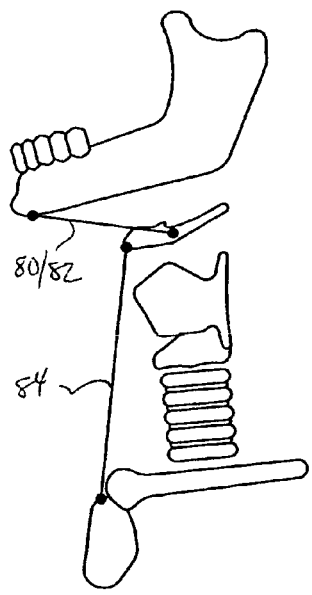
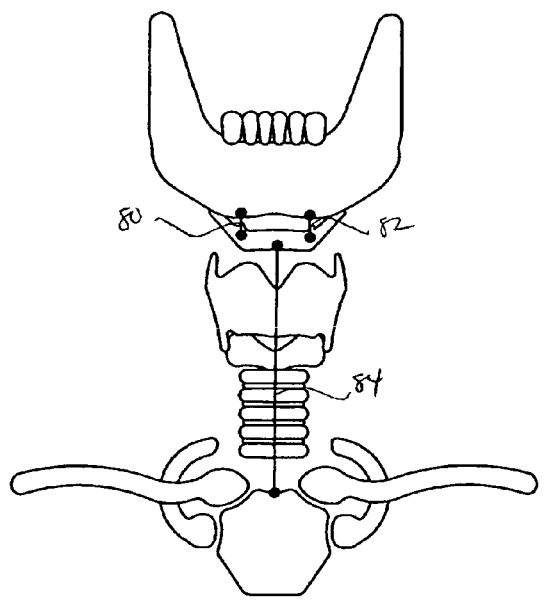
FIG. 8G  FIG. 8H

DEVICES AND METHODS FOR TREATING SLEEP DISORDERS

CROSS REFERENCE TO RELATED APPLICATIONS

This application claims the benefit of U.S. Provisional Application No. 60/685,513, filed May 27, 2005, under 35 U.S.C. § 119(e). This application also claims the benefit of U.S. Provisional Application No. 60/717,337, filed Sep. 15, 2005, under 35 U.S.C. § 119(e). The entire disclosures of both of those provisional applications are incorporated herein by reference.

FIELD OF THE INVENTION

The inventions described herein relate to devices and associated methods for treating sleep disorders. More particularly, the inventions described herein relate to devices and methods for treating sleep disorders such as obstructive sleep apnea, snoring, etc.

BACKGROUND OF THE INVENTION

Obstructive sleep apnea (OSA) is a highly prevalent sleep disorder affecting an estimated 18 million people in the United States, and an estimated 36 million people world wide. Furthermore, the affected population is estimated to be growing at 22% per annum. OSA is not just a quality of sleep issue. OSA has several co-morbidities that drive treatment, including heart failure, hypertension, myocardial infarction, stroke, and diabetes. Despite the seriousness of the condition, it is estimated that only 5% to 8% of the affected population have been diagnosed and treated.

Approximately 80% of the patients diagnosed with OSA are prescribed continuous positive airway pressure (CPAP) therapy. Although CPAP is the first line of treatment for the majority of patients and is considered the gold-standard by most practitioners, it enjoys only 30-60% average patient compliance. Approximately 10- 15% of patients will have surgical treatment, but the surgical options tend to be invasive and are not always effective. Approximately 5- 10% of patients will use a mandibular advancement device, but such devices tend to have limited efficacy and are often associated with joint pain.

Thus, there is a need for improved OSA treatment devices in terms of patient compliance, invasiveness and efficacy.

SUMMARY OF THE INVENTION

To address these and other unmet needs, the present invention provides, in exemplary non-limiting embodiments, devices and methods for treating OSA and other sleep disorders. Exemplary embodiments are described in more detail hereinafter.

Some of the embodiments described herein may act directly or indirectly on tissues of the upper airway, including the oropharynx and/or hypopharynx, to increase the luminal size thereof or otherwise open the airway to mitigate against or reverse a compromise of airflow such as a hypopnea event, an apnea event, a snoring event, etc. The increase in airway size may be in the anterior, inferior and/or lateral directions, for example, and may occur at one or multiple levels. Although described with reference to the pharynx, the embodiments described herein may also be applied to other portions of the airway such as the nasopharynx, larygopharynx, and larynx and associated tissues with similar effect.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings:

FIGS. 7A-7D are schematic illustrations of an alternative resilient traction device;

FIGS. 8C-8N are schematic diagrams of various embodiments of tension members acting on the hyoid bone to achieve the force vectors shown in FIGS. 8A and 8B;

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the invention.

Figure 1A:
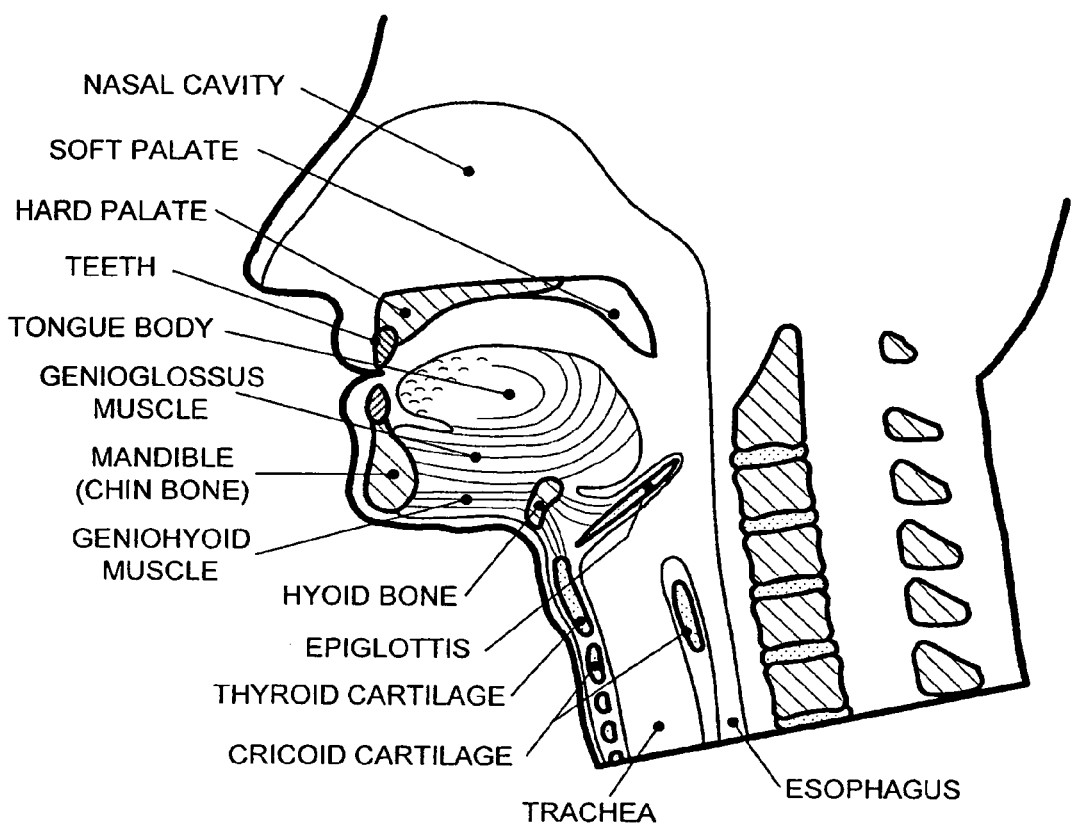
FIGS. 1A and 1B are schematic illustrations of relevant anatomy.
Figure 1B:
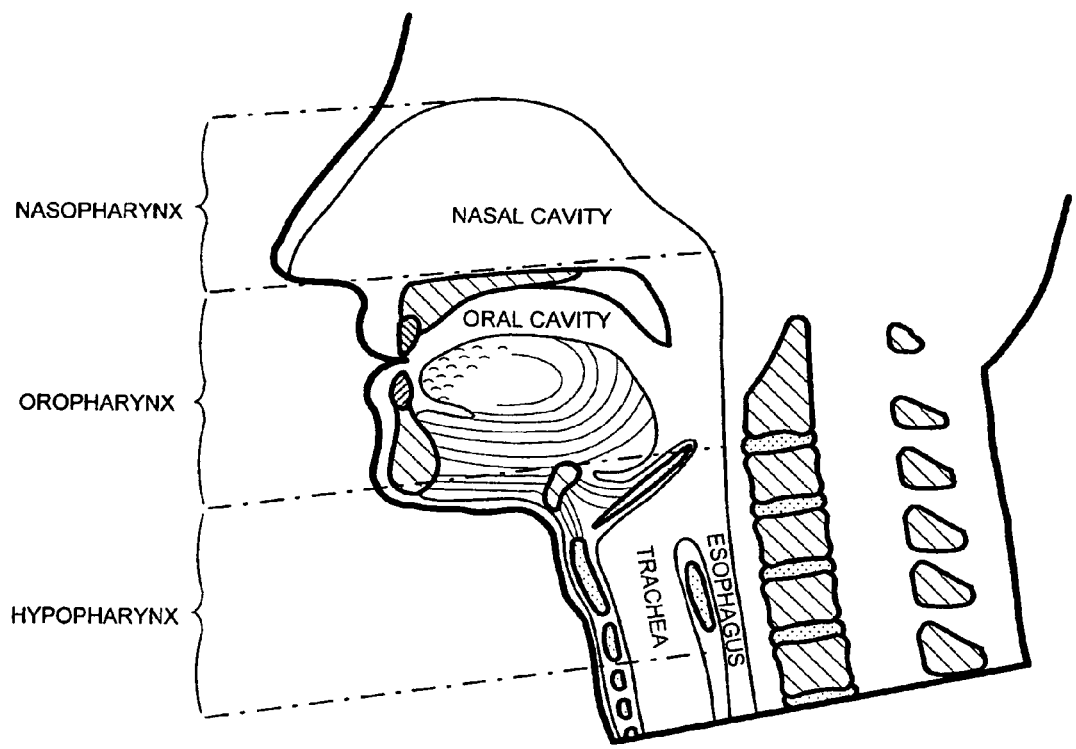

With reference to FIGS. 1A and 1B, some of the anatomical features relevant to the embodiments described herein are schematically illustrated. Other anatomical features may be discussed hereinafter but not specifically illustrated or labeled. In such instances, reference may be made to Gray's Anatomy and/or Netter's Atlas of Human Anatomy for an understanding thereof.

Figure 2A:
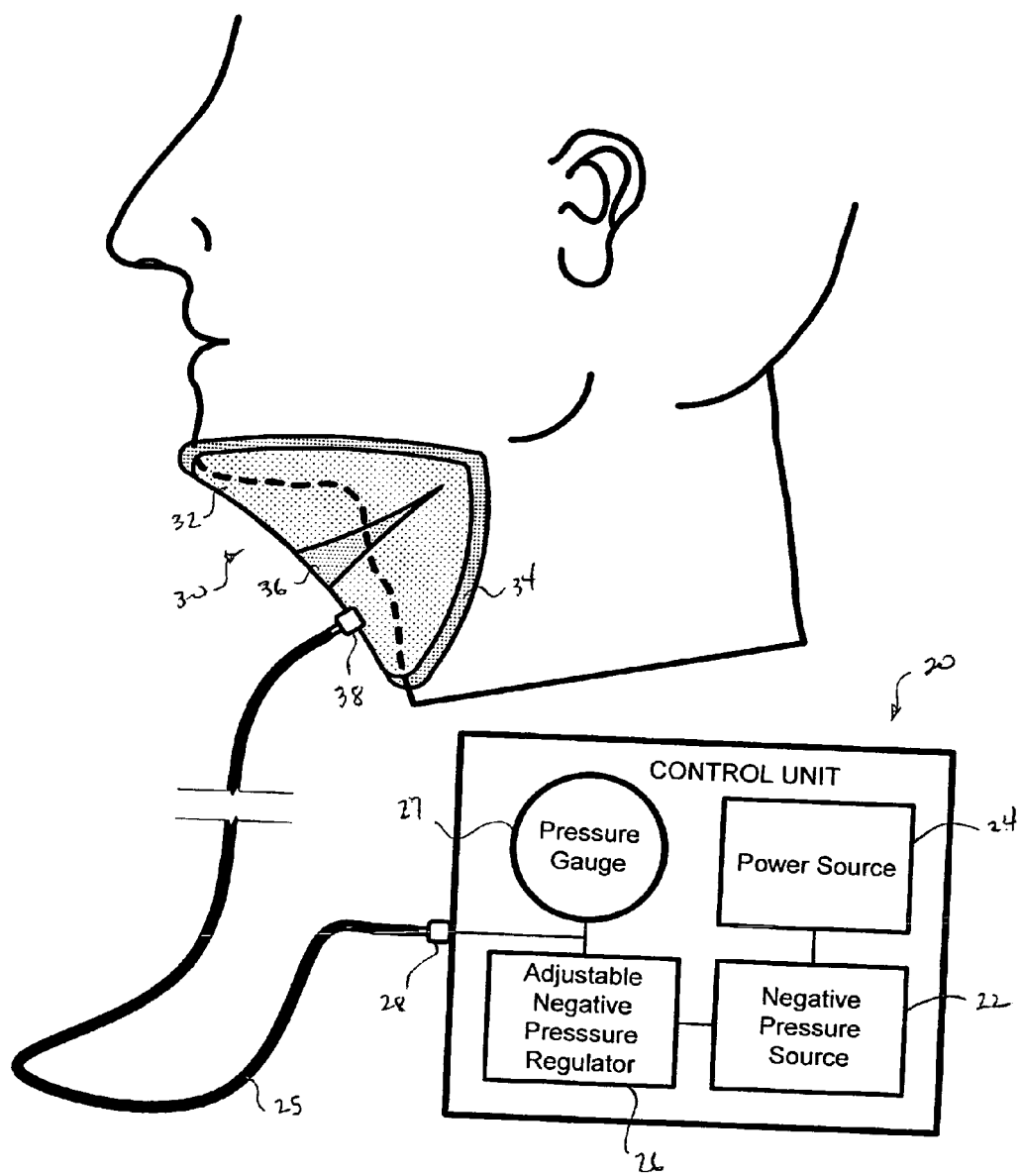
FIGS. 2A and 2B are schematic illustrations of a negative pressure system shown disposed on a patient.
Figure 2B:
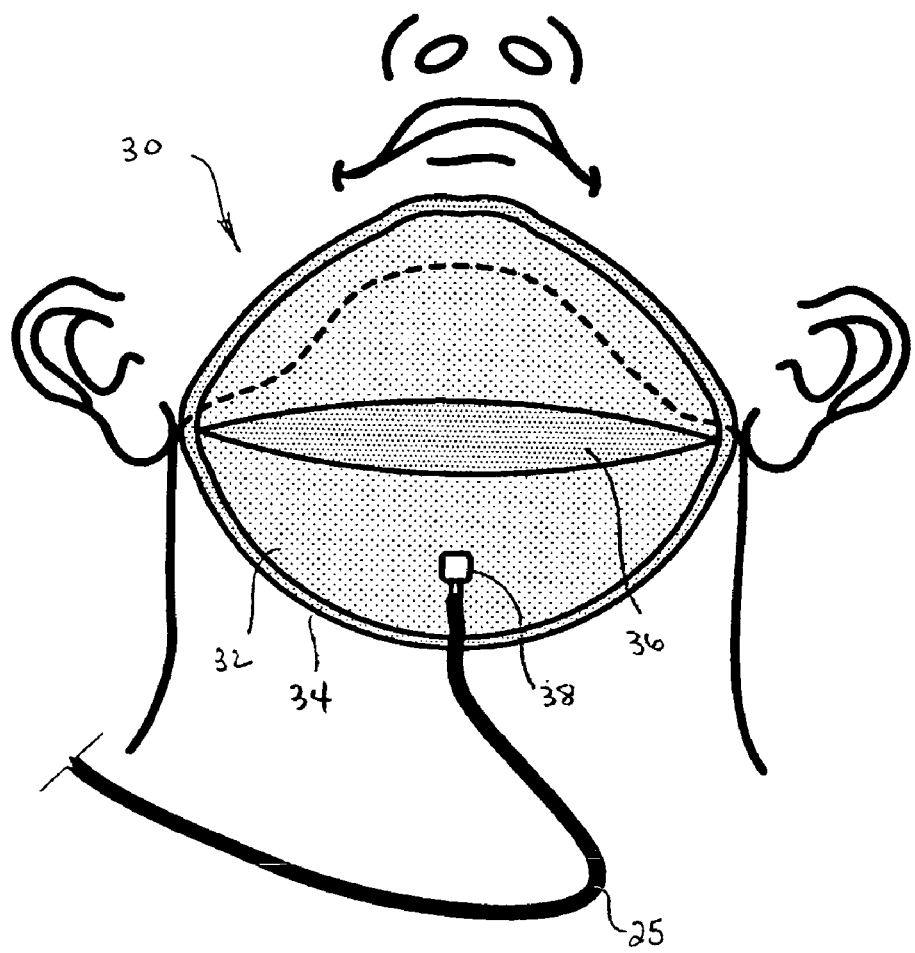

With reference to FIGS. 2A and 2B, a negative pressure system is shown. The negative pressure system includes a neck appliance 30, shown disposed on the neck and under the jaw, and a source of controlled negative pressure 20. The neck appliance 30 generally includes a body portion 32 and a perimeter seal 34. The body portion 32, the perimeter seal 34 and the patient's skin thereunder define a negative pressure zone effecting tissues under the mandible and around the neck as will be described in more detail hereinafter. A port 38 provides fluid communication through the body portion 32 to the negative pressure zone for evacuation thereof.

Figure 4A:
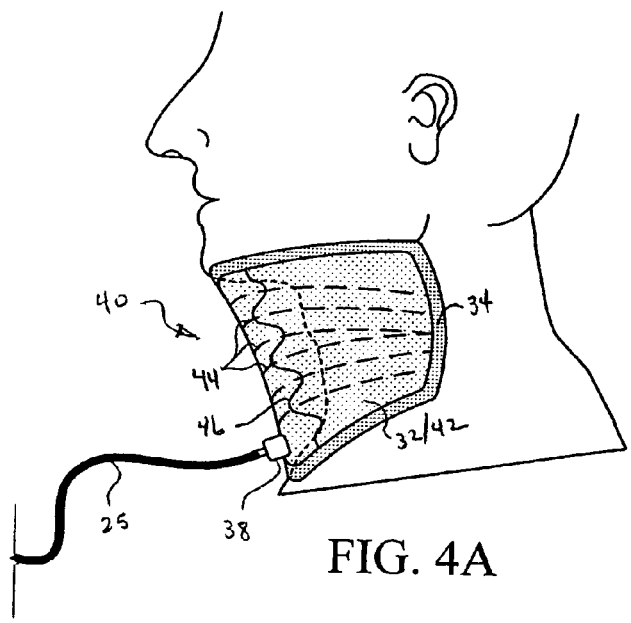
FIGS. 4A-4C are schematic illustrations of alternative negative pressure devices shown disposed on a patient.
Figure 4B:
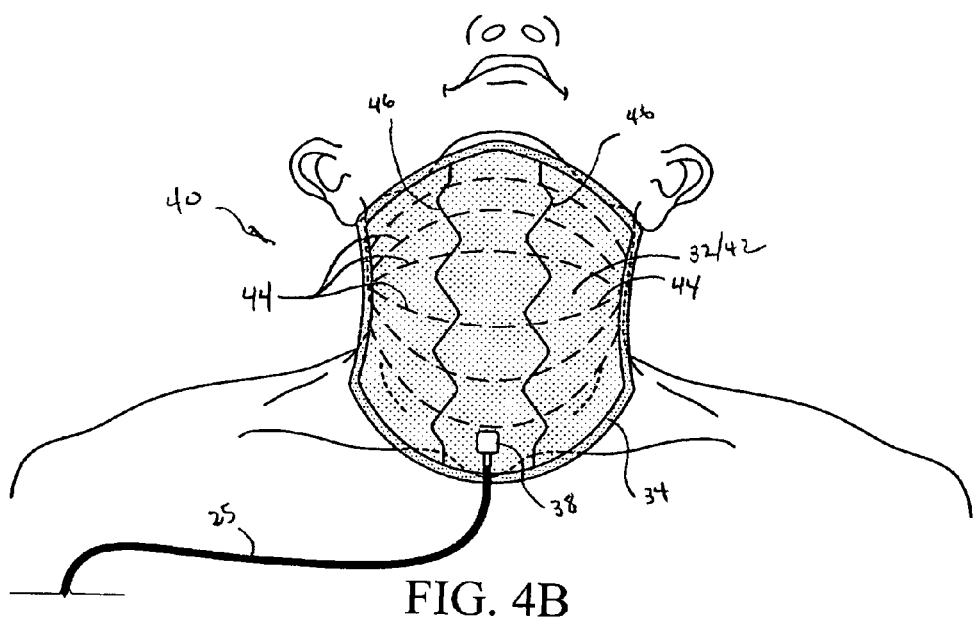
Figure 4C:
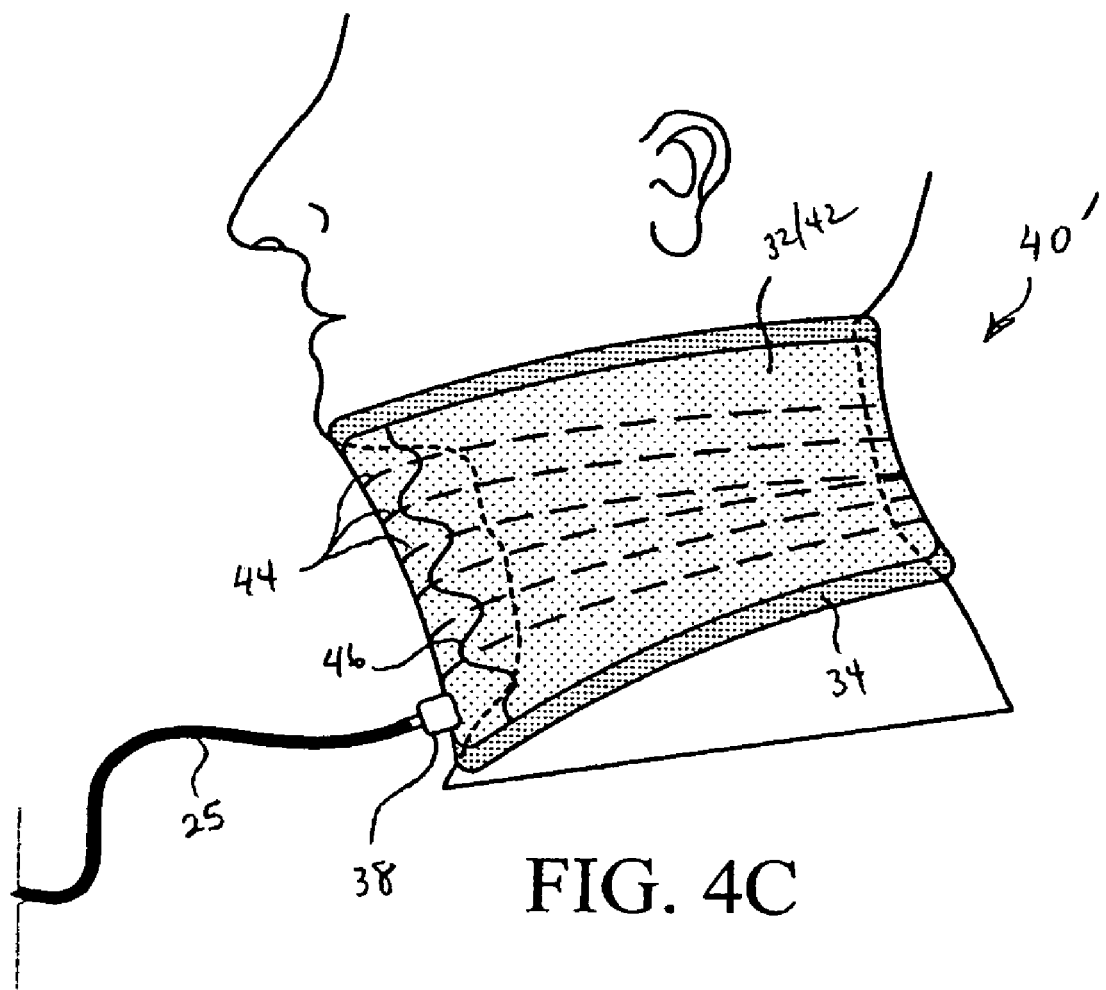

The body portion 32 has sufficient structural integrity to resist collapse due to the negative pressure gradient between the negative pressure zone inside the device and the atmosphere outside the device. The body portion 32 is also impermeable or semi-permeable to gas (e.g., air) within the desired pressure range (e.g., 0.01-14.7 psi). The body portion 32 may comprise, for example, a rigid shell, a semi-rigid shell, or a flexible shell as shown in FIGS. 2A and 2B, or a bellows structure as shown in FIGS. 4A-4C.

With continued reference to FIGS. 2A and 2B, the body portion 32 is shown as a shell comprising, for example, a thermoplastic polymer (e.g., ABS) formed by vacuum molding, injection molding, stereo-lithography or fused deposition modeling. If a rigid or semi-rigid shell is used for the body portion 32, a sealed hinge 36 (such as a cut-out from the shell covered by an impermeable or semi-permeable membrane) may be utilized to permit relative articulation of the user's head and neck while maintaining the negative pressure zone.

The perimeter seal 34 provides a gas seal between the body portion 32 and the user's skin. The perimeter seal 34 may comprise, for example, low durometer closed cell foam such as PVC adhesively bonded to the body portion 32, for example. Alternatively, the perimeter seal 34 may comprise a sealing tape partially overlapping the body portion 32 and partially overlapping the user's skin.

The body portion 32 and the perimeter seal 34 provide a sufficient seal to maintain the desired level of negative pressure in the negative pressure zone. The body portion 32 and the perimeter seal 34 may be air-tight (impermeable) or may have a limited and/or controlled leak rate (semi-permeable). Generally, the more the permeable the body portion 32 and the perimeter seal 34 are, and/or the more leaky the perimeter seal 34 is, the greater the evacuation flow rate required to compensate for leakage in order to maintain the desired level of negative pressure.

A negative pressure control unit 20 is coupled to the neck appliance 30 via a fluid line or tube 25 connected to port 38 on the neck appliance 30 and port 28 on the control unit 20. The control unit 20 may generally include a negative pressure source 22 (e.g., vacuum pump), which may be electrically powered by a power source 24 (e.g., DC battery or 120V AC line power). The negative pressure source 22 may be connected to an adjustable regulator 26 to titrate the amount of negative pressure applied to the neck appliance 30. The regulator 26 may include a vent (not shown) which enables it to function as a pressure regulator. Alternatively, the regulator 26 may function as a flow regulator and a negative pressure relief valve may be incorporated into the neck appliance 30 and/or line 25 to maintain the desired level of negative pressure. Those skilled in the art will recognize that a variety of devices (valves, regulators, etc.) may be plumbed into the system to achieve and maintain the desired level of negative pressure. Further, the control unit may be configured to deliver constant, intermittent or feedback controlled negative pressure. Feedback parameters include, for example, oxygen saturation, plural cavity pressure, inhalation/exhalation flow, snore volume, etc., and suitable sensors may be employed accordingly.

Figure 3C:
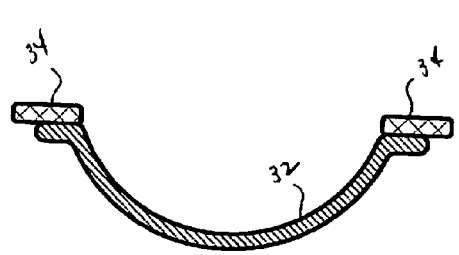
FIGS. 3A-3D are side, front, and cross-sectional views of the negative pressure device shown in FIGS. 2A and 2B.
Figure 3A:
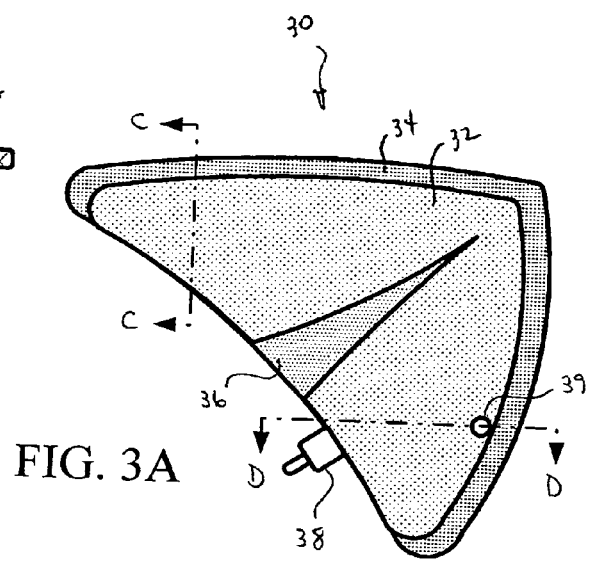
Figure 3B:
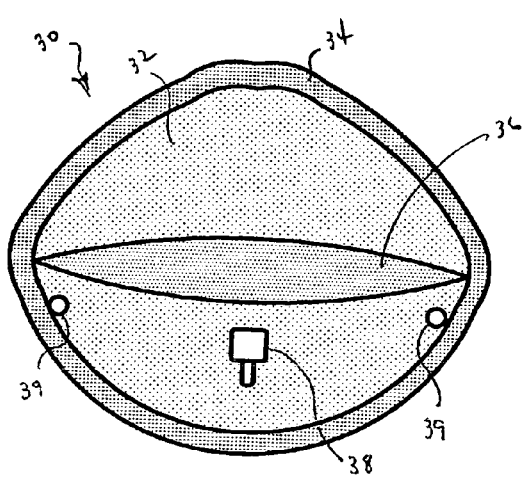
Figure 3D:
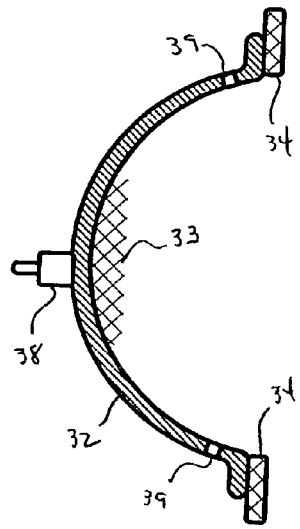

With reference to FIGS. 3A-3D, the neck appliance 30 is shown in more detail. FIG. 3A is a side view, FIG. 3B is a front view, and FIGS. 3C and 3D are cross-sectional views taken along lines C-C and D-D in FIG. 3A. From these views, it may be appreciated that the body portion 32 may have concave interior shape to accommodate expansion of tissue upon application of negative pressure. Alternatively, as shown in FIGS. 4A-4C, the body portion 32 may have a shape that generally follows the contour of the user's neck with a stand-off sufficient to accommodate expansion of tissue in the negative pressure zone.

With continued reference to FIGS. 3A-3D, an optional diffuser 33 such as an open-cell foam may be placed on the inside of the shell 32 over the port 38 to prevent skin from occluding the port if the suction displaces the skin sufficiently to otherwise come into contact with the shell 32. Also optionally, small vent holes 39 may be proved to permit limited infusion of air to provide a cooling effect to the skin in the negative pressure zone. Vent holes 39 may have a diameter of approximately 0.010 inches, for example, to provide the venting function without compromising the ability to draw sufficient vacuum in the negative pressure zone. Alternatively, the shell 32 and/or the perimeter seal 34 may be semi-permeable or otherwise provide for controlled leakage to provide the same venting and cooling function.

With reference to FIGS. 4A-4C, alternative neck appliances 40 and 40' are shown schematically. In the embodiments illustrated in FIGS. 4A and 4C, the body portion 32 is shown as a bellows structure, whereas in the embodiment illustrated in FIGS. 2A-2B and 3A-3D, the body portion 32 is shown as a shell. The neck appliance 40 shown in FIGS. 4A and 4B extends around the anterior and lateral aspects of the neck, and the neck appliance 40' shown in FIG. 4C further extends around the posterior aspect of the neck, thus encircling the neck. The upper portions of the perimeter of neck appliances 40 and 40' generally follow the contour of the mandible. At least a portion of the upper perimeter of the neck appliances 30, 40 and 40' may extend under at least a portion of the mandible such the chin to apply upward forces against the mandible to bias the jaw to the closed position. To bias the jaw to the closed position, neck appliances 40 and 40' may engage the sternum and/or clavicle as best seen in FIG. 4B.

With continued reference to FIG. 4A-4C, the bellows structure 32 may comprise a flexible membrane 42 covering or encasing a plurality of wire or polymeric semi-circular struts 44 that have sufficient hoop strength to resist collapse under negative pressure but permit relative articulation of the user's head and neck. To counteract the tendency of negative pressure to cause the head and neck to nod forward, one or more biasing members 46 such as springs my be incorporated between the upper and lower perimeter portions.

In the embodiments that utilize negative pressure, the zone of reduced pressure may act directly on the skin and indirectly on the subcutaneous tissues, glossal muscles, suprahyoid muscles, infrahyoid muscles and adjacent pharyngeal tissues defining the pharynx (e.g., oropharynx and/or hypopharynx) to indirectly increase the size of the airway. The negative pressure zone may indirectly act on the anterior, inferior and/or lateral aspects of the pharyngeal tissues to increase the size of the airway defined thereby. Thus, the negative pressure zone may apply forces in the anterior, inferior and/or lateral directions. These "pulling" forces may act to increase the luminal size of the upper airway or otherwise open the airway to mitigate against or reverse a compromise of airflow such as a hypopnea event, an apnea event, a snoring event, etc.

Explained differently, by application of negative pressure to tissues outside the upper airway, the magnitude of the pressure gradient between the atmosphere and the airway that normally occurs during inhalation is reduced. Thus, just as positive internal airway pressure (e.g., CPAP) "pushes" pharyngeal tissues outward to open the upper airway, negative external airway pressure "pulls" pharyngeal tissues outward to have the same or similar net effect.

In order to apply "pull" forces in the anterior, lateral and/or inferior directions to tissues adjacent the upper airway, opposing "push" forces must be supported by some anatomical structure or offset by an equal and opposite pull force. For example, the embodiments illustrated in FIGS. 2A-2B and 4A-4B pull pharyngeal tissues anteriorly and inferiorly (forward and down), as well as laterally. The anterior and inferior pull forces may be supported anatomically by pushing on the mandible (e.g., lower jaw and/or chin) and on the sternal head of the sternocleidomastoid muscle and/or thyroid cartilage. Alternatively, as shown in FIGS. 4A and 4B, the anterior and inferior pull forces may be supported anatomically by pushing on the mandible and the sternum and/or bilaterally to the clavicle. The lateral pull forces are offset (in part) by equal and opposite pull forces acting on the right and left sides of the neck, and supported anatomically (in part) by pushing on the mandible and lateral neck muscles (e.g., sternocleidomastoid, scalene, and/or trapezius muscles). Although not illustrated, the neck appliance may extend around the entire circumference of the neck such that the anterior pull force is offset by an equal and opposite force pulling posteriorly on the back of the neck. Generally, the anatomical structures supporting the opposing push forces should exclude the anatomical structures that influence airflow in the upper airway, such as the hyoid bone, the glossal, suprahyoid and infrahyoid muscles, and the adjacent pharyngeal tissues.

Figure 5A:
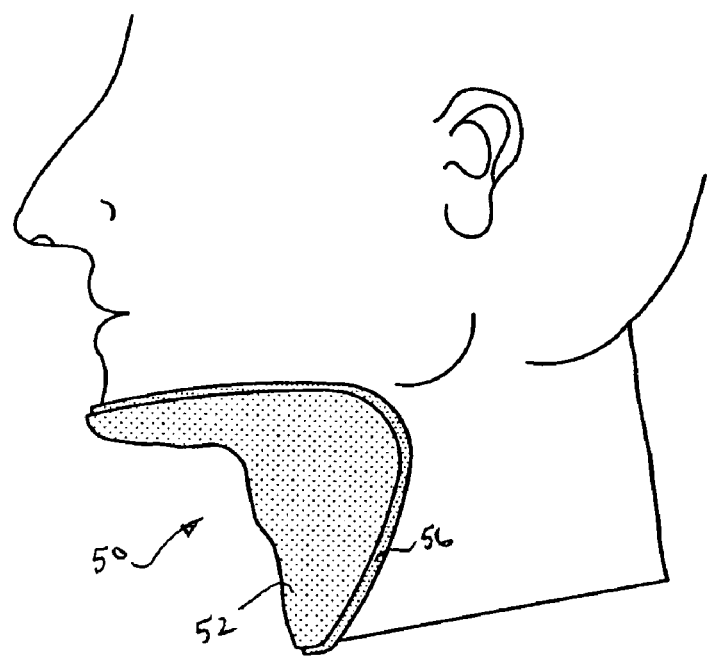
FIGS. 5A-5D are schematic illustrations of adhesive traction devices.
Figures 5B, 5C:
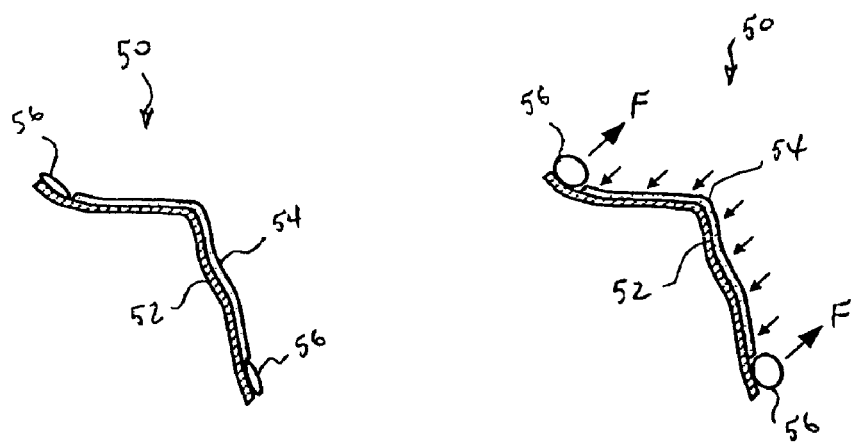

With reference to FIGS. 5A-5C, an inflatable adhesive traction device 50 is shown schematically. Traction device 50 includes a body portion 52 comprising a rigid or semi-rigid shell, for example, having a geometry that generally follows the contours of the user's neck and underside of the mandible. The body portion 52 may extend from the mandible superiorly, to the sternum/clavicle inferiorly. A releasable adhesive layer 54 is bonded or otherwise connected to the inside surface of the shell 52 and is configured to adhesively connect to the user's skin. A single or series of inflatable perimeter balloons 56 is connected to the perimeter of the shell 52. The balloon(s) 56 are inflatable between a collapsed state as shown in FIG. 5B and an expanded state as shown in FIG. 5C.

Upon inflation of the balloon(s) 56, the balloon(s) 56 push on the user's mandible, lateral neck muscles, and sternum/clavicle regions, causing the shell 52 to be displaced in an anterior and inferior direction, thus applying traction to tissues in contact with the adhesive layer 54 in the same direction. Thus, by virtue of the adhesive connection between the shell 52 and the skin of the neck, inflation of the balloon(s) 56 causes traction to be applied to the neck in inferior and anterior directions similar to the forces applied by the negative pressure embodiments described previously, and with similar effect. Applying traction to the skin transfers forces to the underlying platysma muscle which acts to apply negative pressure to the underlying musculature and laryngeal tissues thus opening the airway.

Figure 5D:
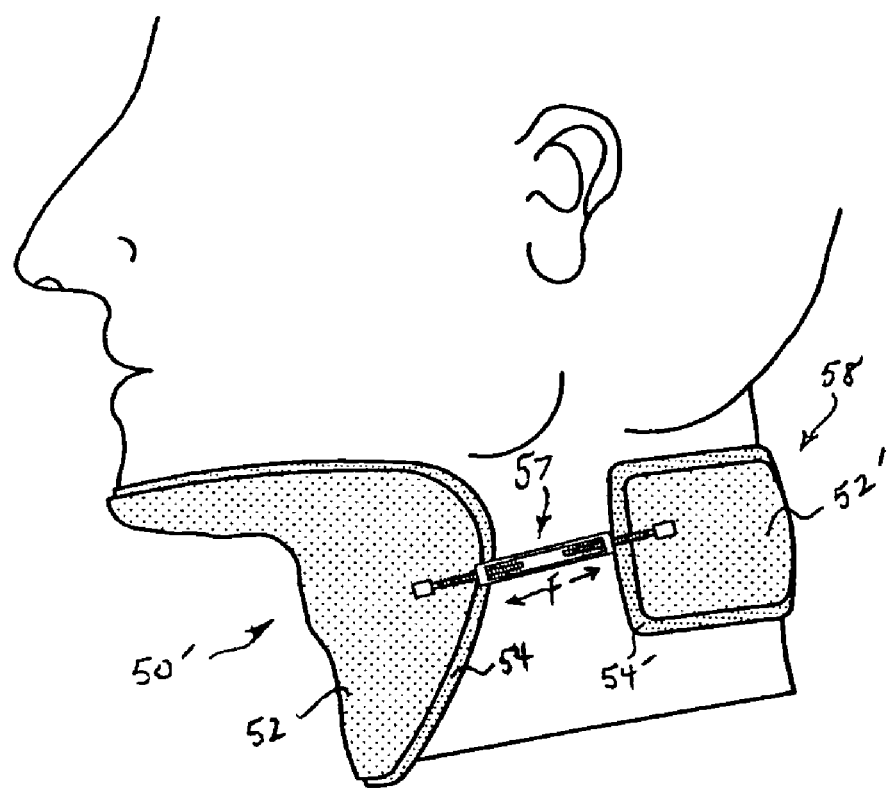

With reference to FIG. 5D, an alternative adhesive traction device 50' is shown schematically. Traction device 50' is similar to device in form and function to device 50 except that forces are applied by a posterior portion 58 rather than balloons 56 as shown previously. Accordingly, device 50' includes a shell 52 and an adhesive layer 54, but may exclude balloon 56. Posterior portion 58 includes a releasable adhesive layer 54' is bonded or otherwise connected to the inside surface of the shell 52' and is configured to adhesively connect to the user's skin on the back of the neck. A traction mechanism 57 such as a turnbuckle interconnects the device 50' to the posterior portion 58. Adjusting the traction mechanism 57 causes the shell 52 to be displaced in an anterior and inferior direction, thus applying traction to tissues in contact with the adhesive layer 54 to have a similar effect as device 50.

Figure 6A:
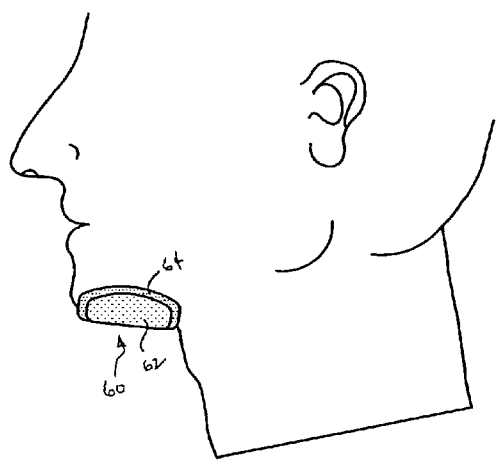
FIGS. 6A-6D are schematic illustrations of a resilient traction device.
Figure 6B:
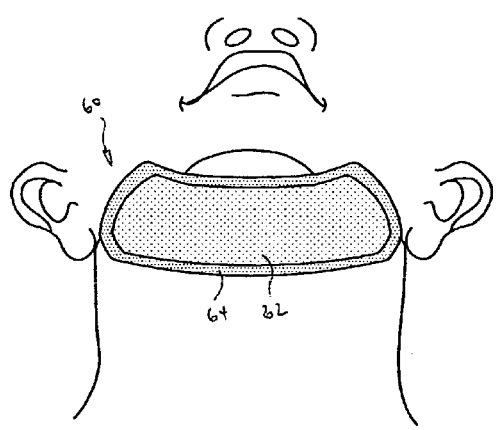
Figure 6C:
Figure 6D:

With reference to FIGS. 6A-6D, a resilient traction device 60 is shown schematically. The resilient traction device 60 includes a flexible and resilient strip 62 formed of sheet metal, for example, which may have a resting profile as schematically shown in FIG. 6C. The device 60 also includes a releasable adhesive layer 64 that is bonded or otherwise connected to the inside surface of the resilient strip 62 and is configured to adhesively connect to the user's skin. Upon application to the neck of the user under the mandible, the resilient strip 62 elastically deforms to conform to the contours of the neck with an applied profile as schematically shown in FIG. 6D. By virtue of the adhesive connection between the strip 62 and the skin of the neck, the elastic bias of the flexible strip 62 causes traction to be applied to the neck by pushing under the mandible in an inferior direction similar to the inferior forces applied by the negative pressure embodiments described previously, and with similar effect. Applying traction to the skin transfers inferior forces to the underlying musculature which acts to apply negative pressure to the underlying laryngeal tissues thus opening the airway.

With reference to FIGS. 7A-7D, an alternative resilient traction device 70 is shown schematically. The resilient traction device 70 includes a flexible and resilient strip 72 formed of sheet metal, for example, which may have a resting profile as schematically shown in FIG. 7C. The device 70 also includes a releasable adhesive layer 74 that is bonded or otherwise connected to the inside surface of the resilient strip 72 and is configured to adhesively connect to the user's skin. Upon application around the neck of a user, the resilient strip 72 elastically deforms to conform to the contours of the neck with an applied profile as schematically shown in FIG. 7D. By virtue of the adhesive connection between the strip 72 and the skin of the neck, the elastic bias of the flexible strip 72 causes traction to be applied to the neck by pushing on the thyroid cartilage and applying lateral and anterior pulling forces similar to the lateral and anterior forces applied by the negative pressure embodiments described previously, and with similar effect. Applying traction to the skin transfers inferior forces to the underlying musculature which acts to apply negative pressure to the underlying laryngeal tissues thus opening the airway. Resilient traction devices 60 and 70 may be used alone or in combination to have the desired net effect.

Figure 8A:
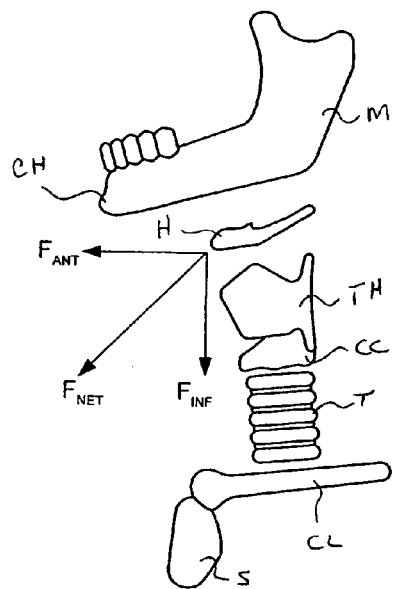
FIGS. 8A and 8B are schematic diagrams illustrating force vectors acting on the hyoid bone.
Figure 8B:
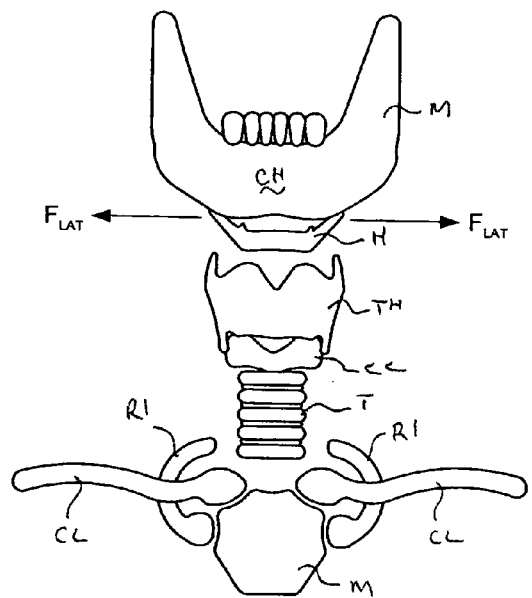

With reference to FIGS. 8A and 8B, force vectors (F) acting on the hyoid bone (H) are schematically illustrated relative to other anatomical features including the mandible (M) and chin (CH) portion thereof, thyroid cartilage (TH), cricoid cartilage (CC), trachea (T), clavicle (CL), sternum (S), and first rib (R1). By pulling the body of the hyoid bone in the anterior and/or inferior directions as shown in FIG. 8A, the luminal size of the airway may be increased or otherwise dilated in the anterior direction. In addition or alternatively, by pulling the greater horns of the hyoid bone in the lateral directions as shown in FIG. 8B, the luminal size of the airway may be increased or otherwise dilated in the lateral directions.

These force vectors acting in the hyoid bone may be implemented in a number of different ways, including, for example, utilizing the tension members described with reference to FIGS. 8C-8N and FIGS. 9A-9E, or utilizing the magnetic devices described with reference to FIGS. 10A-10D.

Various combinations of tension member arrangements are illustrated in FIGS. 8C-8N. These arrangements are provided by way of example, not necessarily limitation, and these arrangements may be taken alone or in combination. Further, for each illustrated tension member, one or more members may be utilized to provide a composite effect.

Figure 8C:
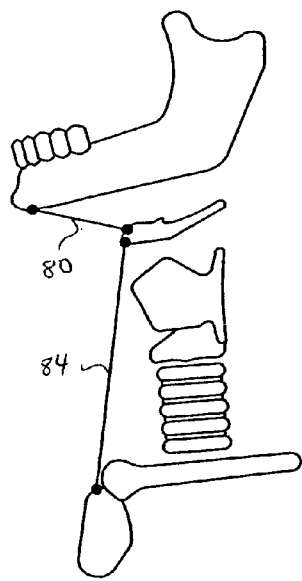
Figure 8D:
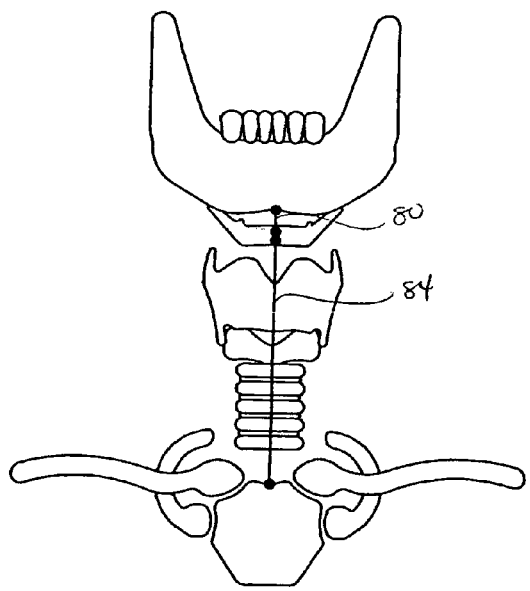

With reference to FIGS. 8C and 8D, a first unilateral tension member 80 is anchored to the middle of the body of the hyoid bone and to the middle of the chin, and a second unilateral tension member 84 is anchored to the middle of the body of the hyoid bone and to the middle of the sternum. Tension members 80 and 84 provide the net force vector illustrated in FIG. 8A.

With reference to FIGS. 8E and 8F, a unilateral tension member 80 is anchored to the middle of the body of the hyoid bone and to the middle of the chin, and bilateral tension members 84 and 86 are anchored to the lateral aspects of body of the hyoid bone near the lesser horns and to the right and left clavicles. Tension members 80, 84 and 86 provide the net force vector illustrated in FIG. 8A. In addition, the lateral placement of tension members 84 and 86 provide the force vectors illustrated in FIG. 8B.

With reference to FIGS. 8G and 8H, bilateral tension members 80 and 82 are anchored to the lateral aspects of the body of the hyoid bone near the lesser horns and to the lateral aspects of the chin, and a unilateral tension member 84 is anchored to the middle of the body of the hyoid bone and to the sternum. Tension members 80, 82 and 84 provide the net force vector illustrated in FIG. 8A. In addition, the lateral placement of tension members 80 and 82 provide the force vectors illustrated in FIG. 8B.

Figure 8I:
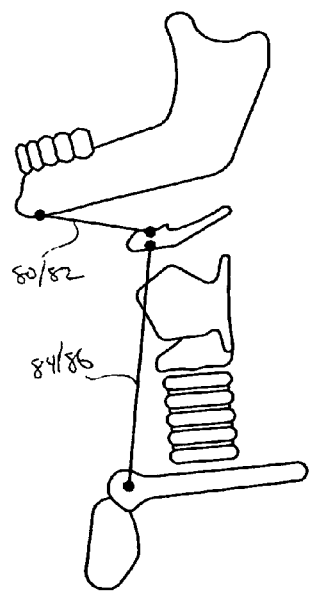
Figure 8J:
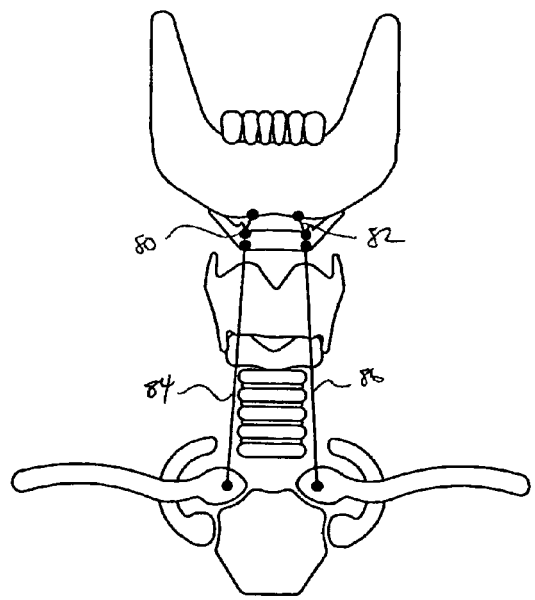

With reference to FIGS. 8I and 8J, bilateral tension members 80 and 82 are anchored to the lateral aspects of body of the hyoid bone near the lesser horns and to the lateral aspects of the chin, and bilateral tension members 84 and 86 are anchored to the lateral aspects of body of the hyoid bone near the lesser horns and to the right and left clavicles. Tension members 80, 82, 84 and 86 provide the net force vector illustrated in FIG. 8A. In addition, the lateral placement of tension members 80, 82, 84 and 86 provide the force vectors illustrated in FIG. 8B.

Figure 8K:
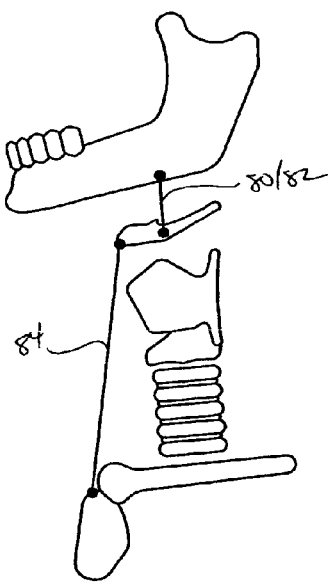
Figure 8L:
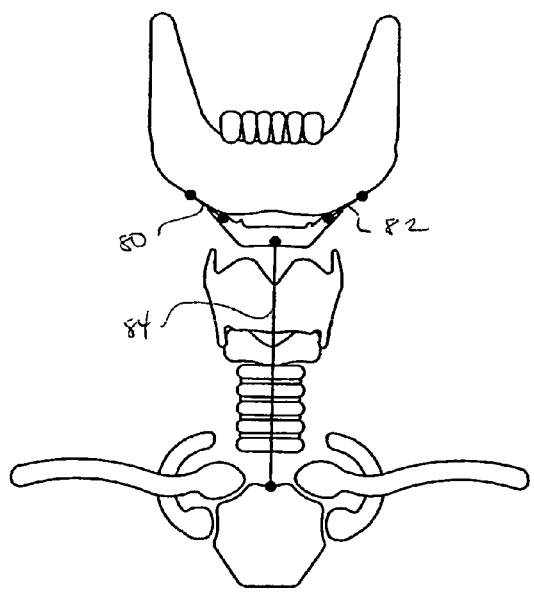

With reference to FIGS. 8K and 8L, bilateral tension members 80 and 82 are anchored near the greater horns of the hyoid bone lateral aspects of the mandible, and a unilateral tension member 84 is anchored to the middle of the body of the hyoid bone and to the middle of the sternum. Tension members 80, 82, and 84 provide the net force vector illustrated in FIG. 8A. In addition, the lateral placement of tension members 80 and 82 provide the force vectors illustrated in FIG. 8B.

Figure 8M:
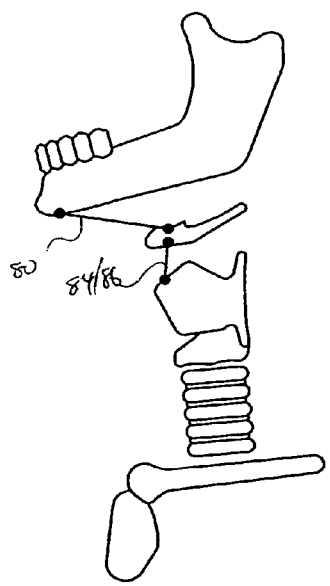
Figure 8N:
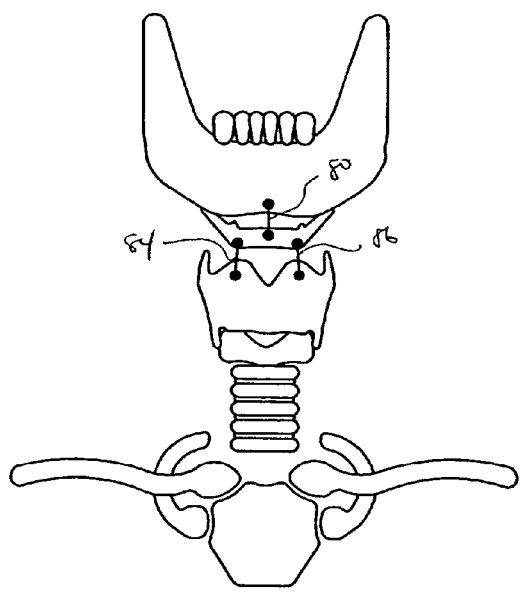

With reference to FIGS. 8M and 8N, a unilateral tension member 80 is anchored to the middle of the body of the hyoid bone and to the middle of the chin, and bilateral tension members 84 and 86 are anchored to the lateral aspects of body of the hyoid bone near the lesser horns and to the lateral aspects of the thyroid cartilage. Tension members 80, 84 and 86 provide the net force vector illustrated in FIG. 8A. In addition, the lateral placement of tension members 84 and 86 provide the force vectors illustrated in FIG. 8B.

With reference to FIGS. 9A-9E, various embodiments of tension members 90 are shown schematically. The tension members 90 may be arranged according to the examples provided in FIGS. 8C-8N. The tension members 90 may be placed surgically by minimal incisions at the attachment or anchor points and tunneling therebetween under the platysma muscle, for example. The tension members 90 may tensioned by adjusting the final implanted length. Tension may be set such that the hyoid is under constant tension or may be set such that the hyoid is under tension only when displaced sufficiently to be concomitant with an apnea or hypoxia event.

Figure 9A:
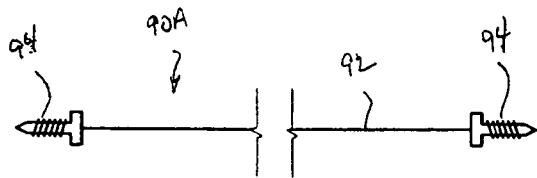
FIGS. 9A-9E are schematic illustrations of various tension members for use in the embodiments shown previously.

In the embodiment illustrated in FIG. 9A, tension member 90A includes a cable 92 that is flexible but relatively inelastic in elongation, such as a polymeric multifilament cable. For example, the cable may comprise a multifilar braided polymeric construction, with filaments of ultra high molecular weight polyethylene (e.g., Spectra™), polyester (e.g. Dacron™), liquid crystal polymers (e.g., Vectran™), or other like polymer, used to form the braided cable. The cable 92 may be covered with an expanded PTFE sheath or other material to facilitate in-growth of tissue. The cable 92 may be connected to the desired anatomical anchor points using screws 94 or other anchor mechanisms conventionally used to anchor to bone and/or cartilage.

Figure 9B:
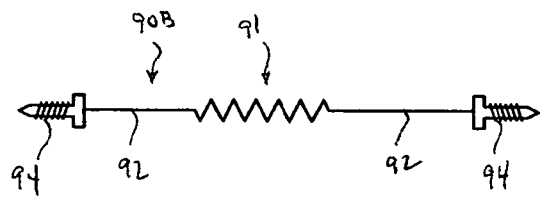

In the embodiment illustrated in FIG. 9B, the tension member 90B includes an elastic member 91 connected in-line with the cable 92 that increases the tension as the length of the tension member 90B increases. Elastic member 91 may comprise an elastic cable material or a spring, for example.

Figure 9C:
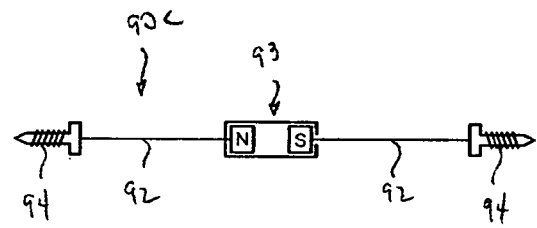

In the embodiment illustrated in FIG. 9C, the tension member 90C includes a magnetic mechanism 93 connected in-line with the cable 92 that increases the tension as the length of the tension member 90C decreases. Magnetic mechanism 93 may comprise two magnets arranged to attract each other and movably disposed in a housing.

Figure 9D:
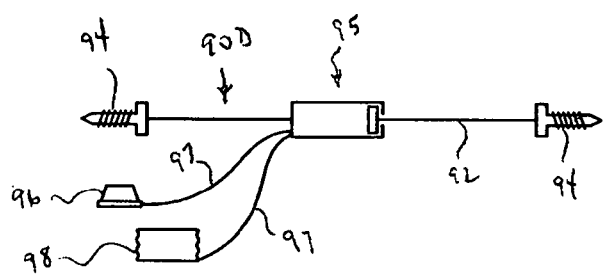

In the embodiment illustrated in FIG. 9D, the tension member 90D includes a pneumatic or hydraulic actuation (e.g., piston and chamber) 95 connected in-line with the cable 92. The actuator 95 may be connected to a subcutaneous injection port 96 or subcutaneous pump 98 via a fluid line 97 to increase or decrease the volume of fluid and pressure in the actuator. The actuator 95 permits adjustment of the length and/or dynamic characteristics of the tension member 90D from outside the body without the need for surgical access.

Figure 9E:
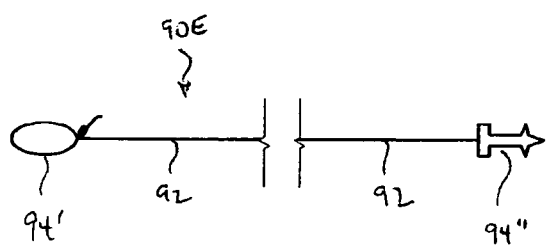

In the embodiment illustrated in FIG. 9E, the tension member 90E includes alternative anchoring mechanisms 94' and 94" for attachment to the hyoid bone. Anchor mechanism 94' comprises a loop or band that may encircle a portion of the hyoid bone, thereby negating the need to mechanically disrupt the bone as with a screw. Anchor mechanism 94" comprises an expandable anchor wherein the expandable portion engages more surface area than otherwise provided by the threads on a bone screw.

With reference to FIGS. 10A-10D, various embodiments of magnetic devices acting on the hyoid bone are schematically illustrated. The illustrated embodiments generally utilize a magnet implanted and attached to the hyoid bone, together with an external magnet which either attracts or repels the implanted magnet. For example, an implanted magnet may be placed on the middle portion of the body of the hyoid bone with external magnets placed on either the front or back of the user's neck as shown to achieve anterior forces acting thereon. Alternatively, the implanted and external magnets may be placed more laterally to achieve lateral forces acting thereon. For example, implanted magnets may be placed on the greater horns of the hyoid bone with external magnets placed on the left and right sides of the user's neck. The external magnet is relatively fixed such that the magnetic fields apply forces to the hyoid bone and cause displacement thereof to increase the size of the airway as described previously.

Figure 10A:
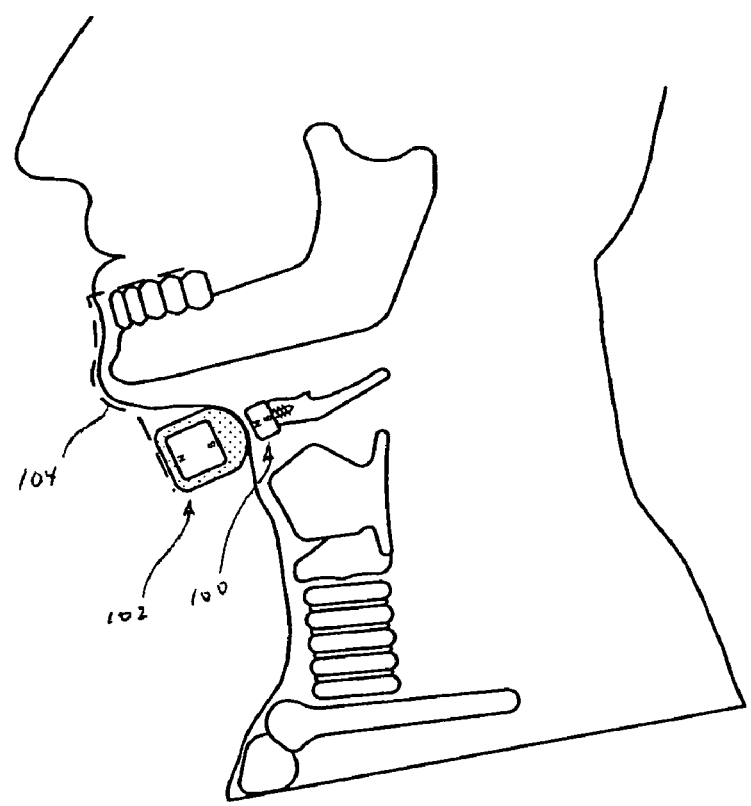
FIGS. 10A-10D are schematic illustrations of magnetic devices acting on the hyoid bone.
Figure 10B:
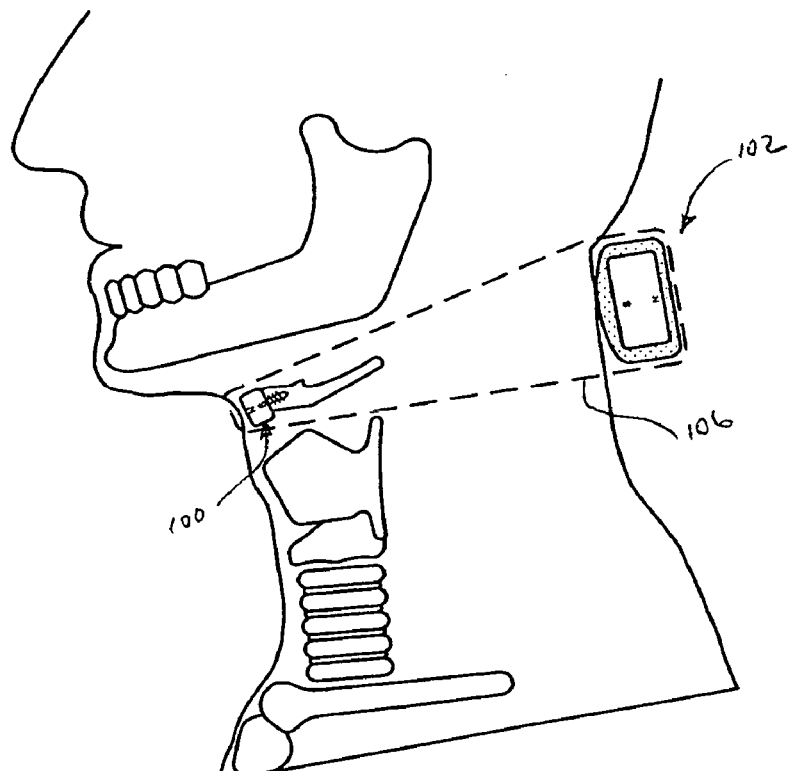

With specific reference to FIGS. 10A and 10B, an implanted magnet 100 is schematically shown anchored to the body of the hyoid bone. Implanted magnet 100 may comprise a rare earth magnetic material such as Neodymium ($Nd_2Fe_{14}B$ or NIB) or Samarium-Cobalt ($SmCo_5$) encapsulated by a non-magnetic biocompatible material and secured to the hyoid bone with a screw, looped band or expandable anchor, for example. An external magnet 102 may be secured to the front of the neck as shown in FIG. 10A to attract the implanted magnet 100, or to the back of the neck as shown in FIG. 10B to repel the implanted magnet 100, both resulting in anterior forces being applied to the hyoid bone. The external magnet 102 may comprise a rare earth magnet as described above, or an electromagnet connected to a suitable power supply (not shown). The external magnet 102 may be surrounded by padding and may be held in position by and oral brace 104 as shown in FIG. 10A or a neck band 106 as shown in FIG. 10B.

Figure 10C:
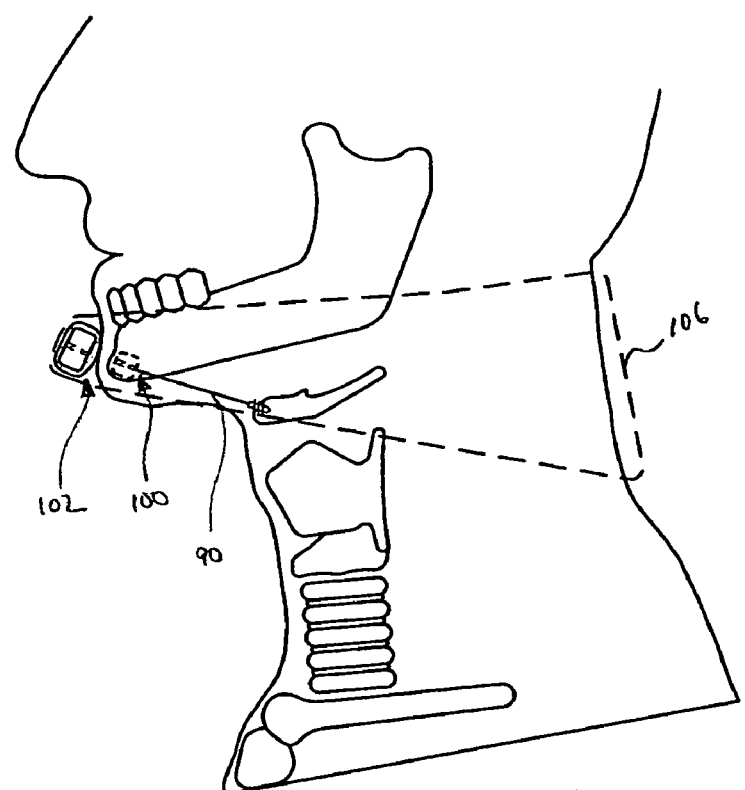
Figure 10D:
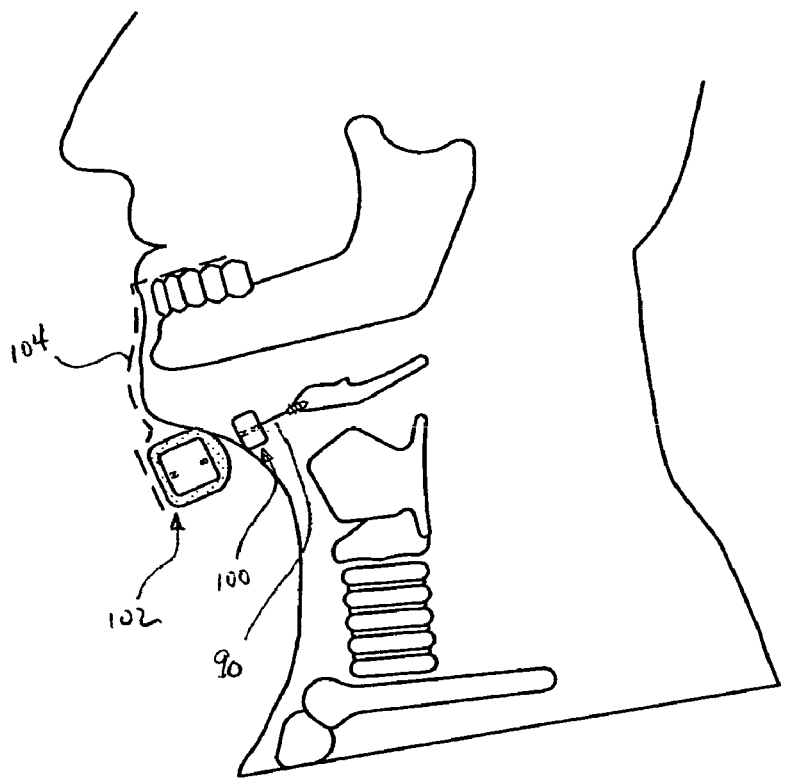

With reference to FIGS. 10C and 10D, the implanted magnet 100 is indirectly connected to the hyoid bone by tension member 90. Utilizing tension member 90 permits the implanted magnet 100 to be positioned more proximate the external magnet 102 independent of hyoid bone position and independent of skin thickness. In the embodiment shown in FIG. 10C, the implanted magnet 100 is positioned proximate the chin inside the mandible and indirectly connected to the hyoid bone via tension member 90. The external magnet 102 is positioned on the chin and held in place with strap 106. In the embodiment shown in FIG. 10D, the implanted magnet 100 is positioned in subcutaneous fat proximate the dermis and indirectly connected to the hyoid bone via tension member 90. The external magnet 102 is positioned under the chin and held in place with oral brace 104.

Figure 11A:
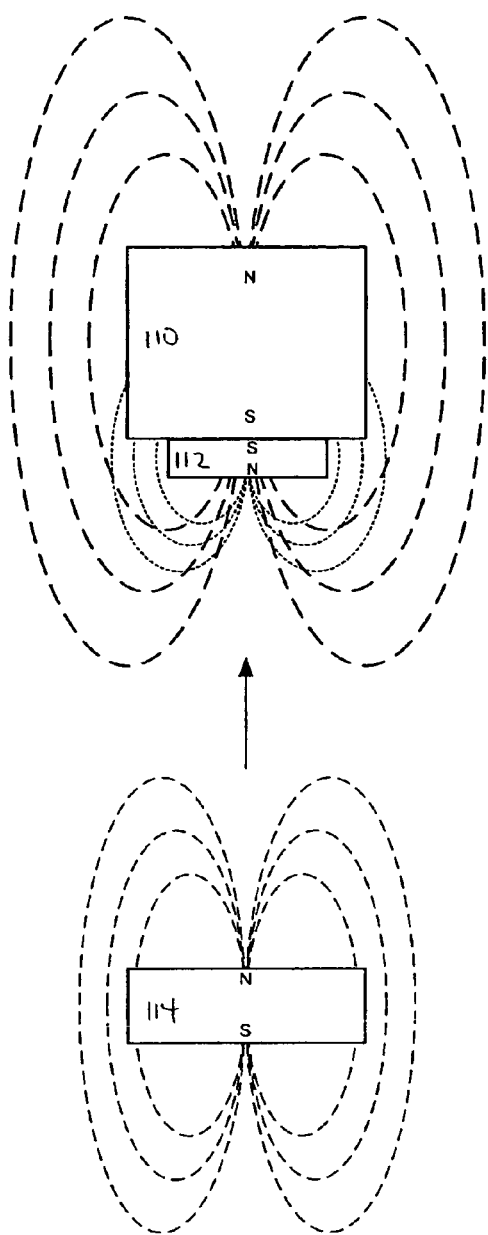
FIGS. 11A and 11B are schematic illustrations of a magnetic arrangement for use in the embodiments illustrated in FIGS. 10A-10D.
Figure 11B:
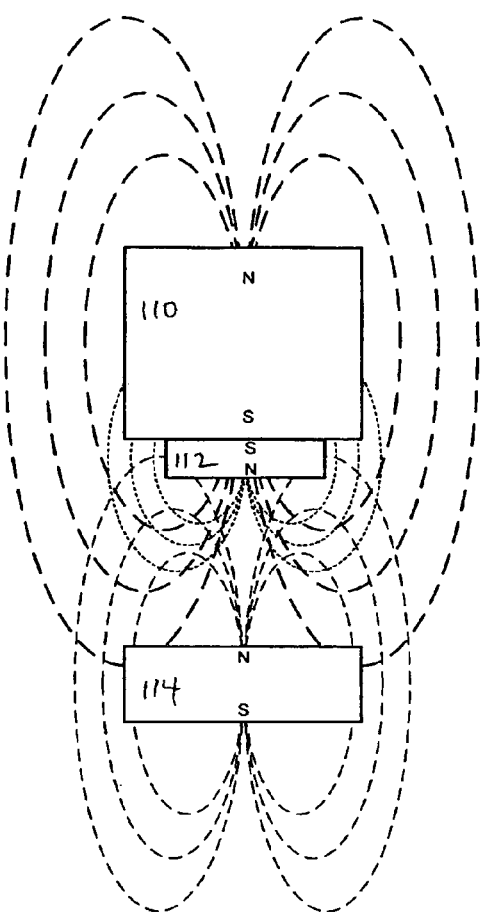

With reference to FIGS. 11A and 11B, an example of a magnetic arrangement for use in the embodiments shown in FIGS. 10A-10D is schematically illustrated. In the illustrated arrangement, two groups of magnets are shown, one comprising magnet 114 and another comprising magnetic pair 110/112. Magnet 114 may correspond to the implanted magnet 100 described previously, with the magnet pair 110/112 corresponding to the external magnet 102 described previously, or vice-versa. The pair of magnets 110 and 112 are physically connected (e.g., adhesively bonded) together, each with either the south or north poles facing each other. Having the same poles facing each other provides a unique magnetic field, but causes the magnets 110 and 112 to repel each other, hence the need for a sufficiently strong physical connection therebetween. Generally speaking, the magnetic field of magnet 110 provides a greater magnetic force than magnet 112.

As magnet 114 is moved toward magnet pair 110/112, the attractive force between magnet 114 and magnet 110 is stronger than the repulsive force between magnet 114 and magnet 112, thus creating a net attractive force as shown in FIG. 11A. As magnet 114 approaches magnet pair 110/112, the attractive force between magnet 110 and 114 is counterbalanced by the repulsive force between magnet 112 and 114, thus creating a zone of zero net force as shown in FIG. 11B. As magnet 114 moves closer to magnet pair 110/112, the repulsive force between magnet 112 and magnet 114 becomes greater than the attractive force between magnet 110 and magnet 114. This arrangement allows attraction between two groups of magnets that decreases to zero as the magnets approach, which may be useful in the embodiments described with reference to FIGS. 10A, 10C, and 10D because it allows for attractive forces to be applied to the hyoid bone without the risk of pinching tissue (e.g., skin) as the magnets come into close proximity.

Figure 12A:
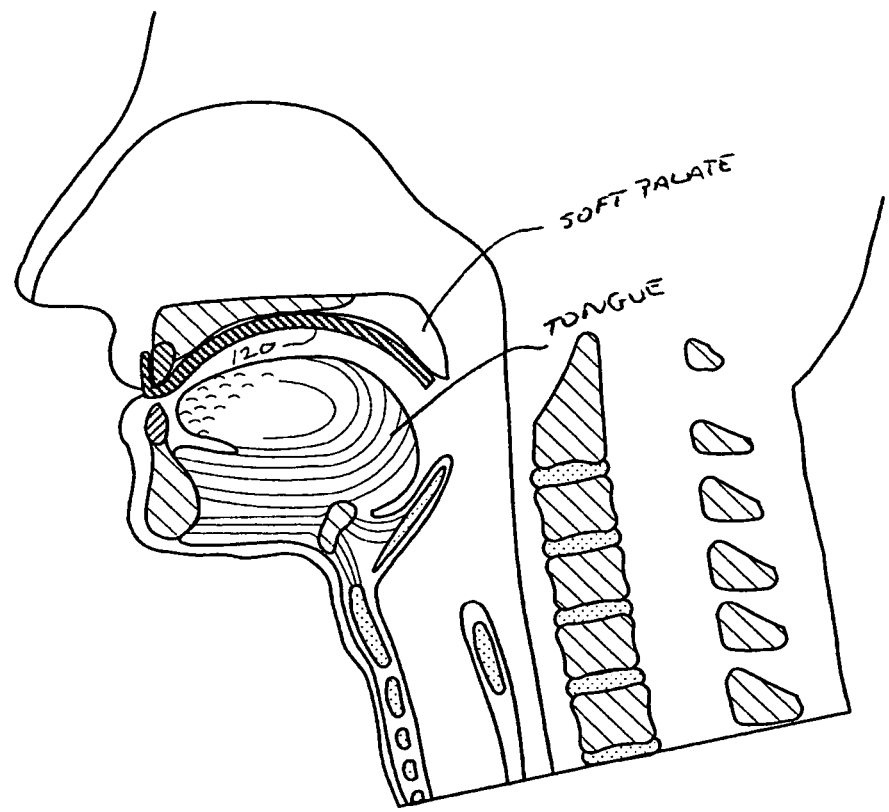
FIGS. 12A-12D are schematic illustrations of intra-oral devices providing an alternative airway passage.
Figure 12B:
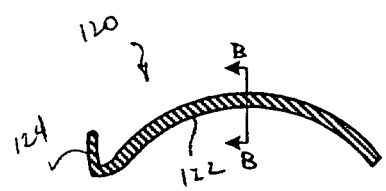
Figure 12C:
Figure 12D:
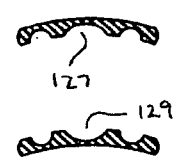
Figure 12E:

With reference to FIGS. 12A-12D, various embodiments of intra-oral devices that provide an alternative airway passage are shown schematically. With specific reference to FIG. 12A, intra-oral device 120 is shown disposed in a user's mouth. Device 120 includes a body portion 122 having a geometry that follows the contours of the roof of the mouth (hard and soft palates) and a retainer portion 124 that partially surrounds one or more teeth to hold the device 120 in place as shown. One or more holes 125, inferior channels 127 or superior channels 129 as seen in FIGS. 12C, 12D and 12E, respectively, extend through the body portion 122 of the device 120 to define a path extending from approximately the retainer portion 124 adjacent the teeth to approximately the distal aspect of the body portion 122 beyond where the tongue naturally rests against the soft palate. The more holes 125, inferior channels 127 or superior channels 129 provide a passage for air to pass through the oral cavity and into the oropharynx despite the tongue pressing against the soft palate and despite the soft palate occluding the nasopharynx.

Figure 13A:
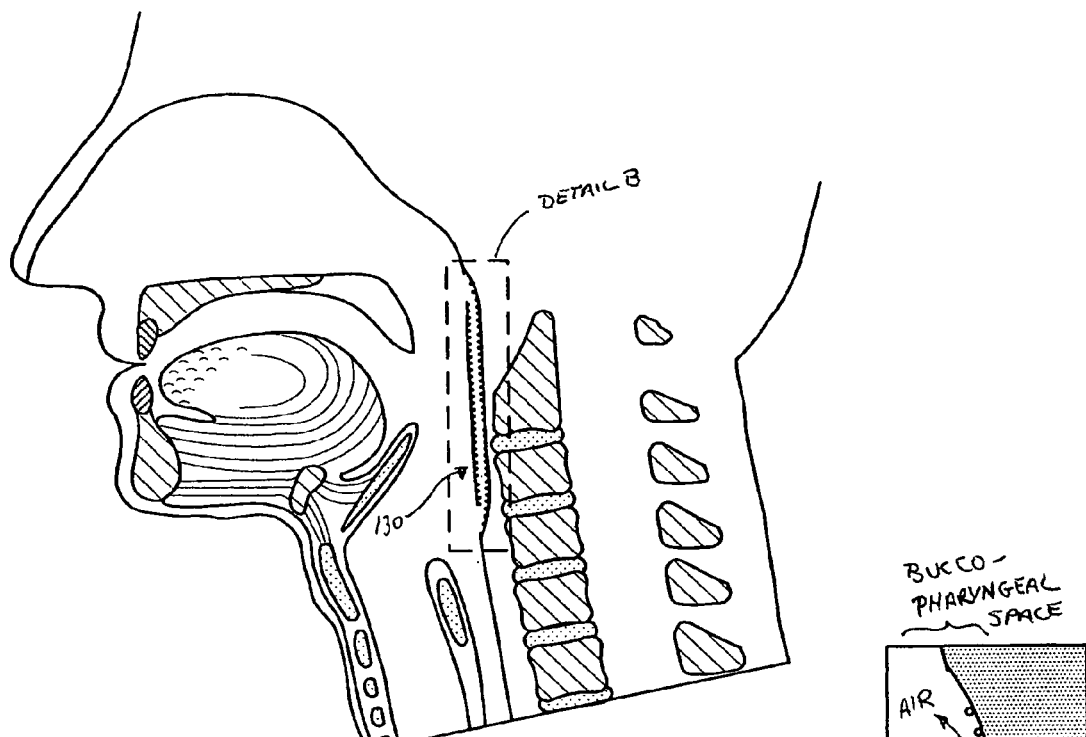
FIGS. 13A and 13B are schematic illustrations of an implantable device providing an alternative airway passage.
Figure 13B:
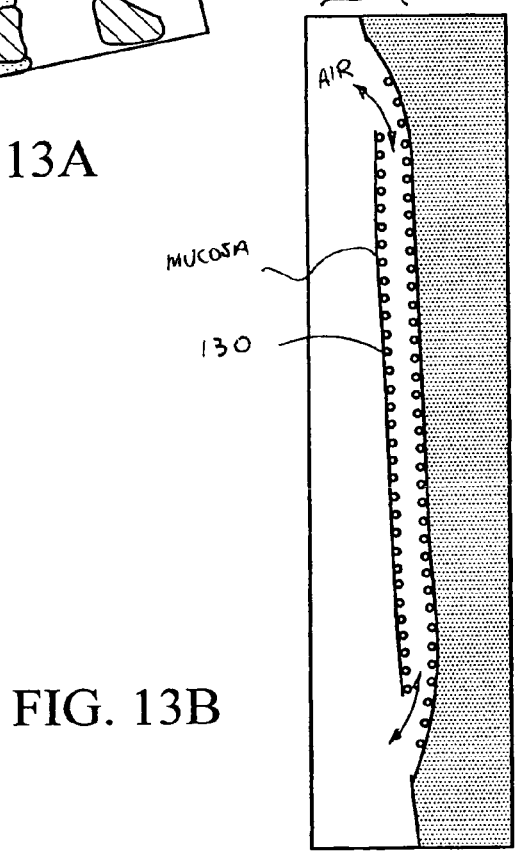

With reference to FIGS. 13A and 13B, an implantable device 130 is shown schematically. Implantable device 130 may comprise a stent-like structure that defines an alternative air passageway. The stent-like device 130 may comprise a stainless steel or nickel titanium alloy wire or cut tube structure (e.g., self-expanding stent or balloon expandable stent design), and may be covered with a graft material such as expanded PTFE or polyester fabric.

The stent-like device 130 may be disposed submucosally in the buccopharyngeal space and extend from the nasopharyngeal level through oropharyngeal level superior to the esophagus as shown. To position the device 130 as such, a submucosal lumen may be formed by surgically or endoscopically tunneling by blunt dissection. The stent-like device 130 may then be deployed in the dissected lumen, such as by catheterization, for example. Once in place, the device 130 maintains patency of a lumen to provide an alternative air passageway that is useful in the event of occlusion of the natural upper airway.

From the foregoing, it will be apparent to those skilled in the art that the present invention provides, in exemplary non-limiting embodiments, devices and methods for treating OSA and other sleep disorders. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A medical device, comprising:
an elongate member having a first end, a second end, and a length in between the first and second ends, wherein the elongate member further includes a housing having first and second magnets movably disposed therein, a first flexible member extending from the first magnet in a direction away from the second magnet, and a second flexible member extending from the second magnet in a direction away from the first magnet, and wherein the first end includes a first anchoring structure and the second end includes a second anchoring structure, and wherein a longitudinal tensile force in the elongate member is configured to increase as the length of the elongate member decreases.

2. The medical device of claim 1, wherein the device is configured to alter the positioning of structure associated with a patient's upper airway.

3. The medical device of claim 2, wherein the structure includes a hyoid bone of the patient.

4. The medical device of claim 2, wherein the structure includes a thyroid cartilage of the patient.

5. The medical device of claim 2, wherein altering the positioning of structure associated with a patient's upper airway opens the patient's upper airway.

6. The medical device of claim 2, wherein the device is configured to treat a sleep disorder.

7. The medical device of claim 1, wherein the medical device is configured to dilate a patient's upper airway by altering the positioning of one of a patient's hyoid bone and thyroid cartilage.

8. The medical device of claim 7, wherein dilating a patient's upper airway includes increasing a luminal size of the patient's upper airway.

9. The medical device of claim 1, wherein the increase in the tensile force corresponds to the decrease in length of the elongate member.

10. The medical device of claim 1, wherein the elongate member includes an expanded PTFE sheath surrounding a portion of the elongate member, the expanded PTFE sheath configured to promote tissue ingrowth.

11. A method for altering a patient's upper airway, comprising:
providing an elongate member having a first end, a second end and a length therebetween, wherein the elongate member further includes a housing having first and second magnets movably disposed therein, a first flexible member extending from the first magnet in a direction away from the second magnet, and a second flexible member extending from the second magnet in a direction away from the first magnet;
securing the first end of the elongate member to a first anatomical structure of the patient's upper airway; and
securing the second end of the elongate member to a second anatomical structure of the patient's upper airway, wherein the second anatomical structure is spaced from the first anatomical structure by a first distance, and wherein a tension in the elongate member is configured to increase as the length of the elongate member decreases.

12. The method of claim 11, wherein the first end includes a first anchoring structure and the second end includes a second anchoring structure.

13. The method of claim 12, wherein one of the first and second anchoring structures is configured to penetrate tissue.

14. The method of claim 11, wherein the one of the first and second anchoring structures is configured to be embedded within tissue.

15. The method of claim 13, wherein one of the first and second anchoring structures includes an elongate member having radially extending projections.

16. The method of claim 12, wherein the second anchoring structure includes a screw, and securing the second end to the second anatomical structure includes inserting the screw into a bone.

17. The method of claim 12, wherein the first anchoring structure has a first configuration, and the second anchoring structure has a second configuration different than the first configuration.

18. The method of claim 12, wherein one of the first and second anchoring structures includes a loop.

19. The method of claim 11, wherein the method further includes adjusting a length of the elongate member.

20. The method of claim 11, wherein one of the first and second anatomical structures includes the patient's mandible.

21. The method of claim 11, wherein the elongate member includes a flexible cable.

22. The method of claim 11, wherein the first anatomical structure is different from the second anatomical structure.

23. The method of claim 11, wherein the elongate member is configured to promote tissue ingrowth.

24. The method of claim 11, wherein the elongate member includes an expanded PTFE sheath surrounding a portion of the elongate member, the expanded PTFE sheath configured to promote tissue ingrowth.

25. The method of claim 11, wherein altering the patient's upper airway includes increasing a luminal size of the airway.

26. A Mthod of maintaining an open airway comprising:
providing a first tension member and a second tension member, each tension member including a first end, a second end, and a length therebetween, wherein each tension member further includes a housing having a first and second magnets movably diposed therein, a first elongate member extending from the first magnet in a direction away from the second magnet, and a second elongate member extending from the second magnet in a direction away from the first magnet;
securing a first end of each tension member to a patient's hyoid bone; and
securing a second end of each tension member to surrounding anatomical structure such that the tension members pull the hyoid bone in anterior and inferior directions, thereby increasing a luminal size of the airway, wherein the tension in the first tension member is configured to increase as the length of the first tension member decreases, and tension in the second tension member is configured to increase as the length of the second tension member decreases.

27. The method of claim 26, wherein the second end of the first tension member is secured to the chin, and the second end of the second tension member is secured to a clavicle.

28. The method of claim 27, wherein the second end of the second tension member is secured to a right clavicle, and a third tension member is provided having a first end secured to the hyoid bone and a second end secured to a left clavicle.

29. The method of claim 26, wherein the first tension member includes an anchor mechanism at each end of the first tension member.

30. The method of claim 29, wherein the anchor mechanism includes at least one of a screw, a loop, and an anchor having an expandable portion.

31. The method of claim 26, wherein at least one of the first and second tension members pull the hyoid bone in a lateral direction.

32. The method of claim 26, wherein the second end of the first tension member is secured to the chin, and the second end of the second tension member is secured to the sternum.

33. The method of claim 26, wherein the second end of the first tension member is secured to a left lateral portion of the chin, a second end of the second tension member is secured to a right clavicle, a third tension member is provided having a first end secured to the hyoid bone and a second end secured to a left clavicle, and a fourth tension member is provided having a first end secured to the hyoid bone and a second end secured to a right lateral portion of the chin.

34. The method of claim 26, wherein the second end of the first tension member is secured to a middle portion of the chin, a second end of the second tension member is secured to a left lateral portion of the thyroid cartilage, and a third tension member is provided having a first end secured to the hyoid bone and a second end secured to a right lateral portion of the thyroid cartilage.

35. The method of claim 26, wherein securing the first and second ends of each tension member comprises creating an incision proximate an anatomical attachment point, threading the tension members through a patient's muscle and tissue, and anchoring the first and second ends to anatomical locations.

36. The method of claim 26, further comprising adjusting the tension in at least one of the tension members.

37. The method of claim 11, wherein the method further includes providing a second elongate member and securing the second elongate member to the patient.

38. A method for treating a sleep disorder, comprising:
providing a tension member having a first end, a second end, and a length in between the first and second ends, wherein the tension member further includes a housing having first and second magnets movably disposed therein, a first elongate member extending from the first magnet in a direction away from the second magnet, and a second elongate member extending from the second magnet in a direction away from the first magnet, and wherein the first end includes a first anchoring structure and the second end includes a second anchoring structure;
securing the first anchoring structure to a first anatomical structure of a patient's upper airway; and
securing the second anchoring structure to a second anatomical structure of the patient's upper airway, wherein securing the second anchoring structure to the second anatomical structure causes the tension member to bias one of the first and second anatomical structures towards the other of the first and second anatomical structures to dilate the patient's upper airway, and wherein tension in the tension member is configured to increase as the length of the tension member decreases.

39. The method of claim 38, wherein the magnet pair is arranged such that north poles of each magnet in the magnet pair face each other.

40. The method of claim 38, wherein the magnet pair is arranged such that south poles of each magnet in the magnet pair face each other.

41. The method of claim 38, wherein the tension member includes an expanded PTFE sheath surrounding a portion of the tension member, the expanded PTFE sheath configured to promote tissue ingrowth.

42. The method of claim 38, wherein one of the first and second anchoring structures is configured to be embedded in tissue.

43. method of claim 38, wherein the method further includes providing a second elongate member and securing the second elongate member to the patient.

44. The method of claim 38, wherein the first anchoring structure has a first configuration, and the second anchoring structure has a second configuration different than the first configuration.

45. The method of claim 38, wherein one of the first and second anchoring structures includes a loop.

46. A method of altering a patient's upper airway, comprising:
providing a device including an elongate member having a first end, a second end, and a length in between the first and second ends, wherein the elongate member further includes a housing having first and second magnets movably disposed therein, a first flexible member extending from the first magnet in a direction away from the second magnet, and a second flexible member extending from the second magnet in a direction away from the first magnet, and wherein a longitudinal tensile force in the elongate member is configured to increase as the length of the elongate member decreases;
securing the first end to a first anatomical structure of the patient's upper airway; and
securing the second end to a second anatomical structure of the patient's upper airway, wherein the second anatomical structure is spaced from the first anatomical structure by a first distance.

47. The method of claim 46, wherein the first end includes a first anchoring structure, and the second end includes a second anchoring structure.

48. The method of claim 46, wherein the elongate member includes an expanded PTFE sheath surrounding a portion of the elongate member, the expanded PTFE sheath configured to promote tissue ingrowth.

49. The method of claim 46, wherein one of the first and second anatomical structures includes a hyoid bone.

50. The method of claim 46, wherein one of the first and second anatomical structures includes a thyroid cartilage.

51. The method of claim 46, wherein one of the first and second anatomical structures includes a chin.

* * * * *

UNITED STATES PATENT AND TRADEMARK OFFICE
CERTIFICATE OF CORRECTION

PATENT NO. : 7,644,714 B2  Page 1 of 1
APPLICATION NO. : 11/438330
DATED : January 12, 2010
INVENTOR(S) : Robert E. Atkinson et al.

It is certified that error appears in the above-identified patent and that said Letters Patent is hereby corrected as shown below:

In claim 11, column 11, line 14, after "end" insert --,--.

In claim 26, column 12, line 1, replace "Mthod" with --method--.

In claim 26, column 12, line 5, delete the second "a".

In claim 26, column 12, line 9, replace "ina" with --in a--.

In claim 39, column 13, lines 24-26, replace "the magnet pair is arranged such that north poles of each magnet in the magnet pair face each other" with --one of the first and second anatomical structures includes a mandible of the patient--.

In claim 40, column 13, lines 27-29, replace "the magnet pair is arranged such that south poles of each magnet in the magnet pair face each other" with --the tension member is configured to promote tissue ingrowth--.

Signed and Sealed this

Twenty-third Day of March, 2010

David J. Kappos
*Director of the United States Patent and Trademark Office*